United States Patent
Crooke et al.

(10) Patent No.: US 6,428,956 B1
(45) Date of Patent: *Aug. 6, 2002

(54) MASS SPECTROMETRIC METHODS FOR BIOMOLECULAR SCREENING

(75) Inventors: Stanley T. Crooke, Carlsbad; Richard Griffey, Vista; Steve Hofstadler, Oceanside, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/076,206

(22) Filed: May 12, 1998

Related U.S. Application Data

(60) Provisional application No. 60/076,534, filed on Mar. 2, 1998.

(51) Int. Cl.[7] .................................................. C12Q 1/68
(52) U.S. Cl. ............................ 435/6; 435/7.1; 530/350; 536/23.1; 436/501
(58) Field of Search ............................ 436/501; 435/6, 435/7.1; 530/350; 536/23.1; 250/282

(56) References Cited

U.S. PATENT DOCUMENTS

| | | | |
|---|---|---|---|
| 5,571,902 A | 11/1996 | Ravikumar et al. | 536/22.1 |
| 5,834,195 A | * 11/1998 | Benkovic et al. | 435/6 |
| 6,221,601 B1 | * 4/2001 | Koster et al. | 435/6 |

FOREIGN PATENT DOCUMENTS

WO   WO 89/12694   12/1989

OTHER PUBLICATIONS

Dunayevskyly, Y.M., et al., "Simultaneous measurement of nineteen binding constants of peptides to vancomycin using affinity capillary electrophoresis–mass spectrometry," *J. Med. Chem.*, 1998, 41, 1201–1204.

Griffey, R.H., et al., "Determinants of aninoglycoside–binding specificity for rRNA by using mass spectrometry," *Proc. Natl. Acad. Sci. USA*, 1999, 96, 10129–10133.

Kempen, E.C., et al., "A method for the determination of binding constants by electrospray ionization mass spectrometry," *Anal. Chem.*, 2000, 72, 5411–5416.

Loo, J.A., "Studying noncovalent protein complexes by electrospray ionization mass spectrometry," *Mass Spectrometry Reviews*, 1997, 16, 1–23.

Cheng, X. et al., "Electrospray Ionizatio with High Performance Fourier Transform Ion Cyclotron Resonance Mass Spectrometry for the Study of Noncovalent Biomolecular Complexes," *Techniques in Protein Chem. VII*, 1996, 13–22.

Przybylski, M. et al., "Mass spectrometric approaches to molecular characterization of protein–nucleic acid interactions," *Toxicology Letts.*, 1995, 82/83, 567–575.

Sannes–Lowery, K.A. et al., "HIV–1 Tat Peptide Binding to TAR RNA by Electrospray Ionization Mass Spectrometry," *Anal. Chem.*, 1997, 69, 5130–5135.

Köster, H. et al., "A Strategy for rapid and efficient DNA sequencing by mass spectrometry,", *Nature Biotechnology*, 1996, 14, 1123–1128.

Amster, "Fourier Transform Mass Spectrometry", *J. Mass Spectrom.*, 1996, 31, 1325–1337.

Anderegg et al., "Mass Spectrometric Characterization of a Protein—Ligand Interaction", *J. Am. Chem. Soc.*, 1995, 117, 1374–1377.

Baca et al., "Direct Observation of a Ternary Complex between the Dimeric Enzyme HIV–1 Protease and a Substrate–Based Inhibitor", *J. Am. Chem. Soc.*, 1992, 114, 3992–3993.

Baczynskyj et al., "Application of Thermally Assisted Electrospray Ionization Mass Spectrometry for Detection of Noncovalent Complexes of Bovine Serum Albumin with Growth Hormone Releasing Factor and Other Biologically Active Peptides", *Rapid Commun. Mass Spectrom.*, 1994, 8, 280–286.

Bayer et al., "Analysis of Double–Stranded Oligonucleotides by Electrospray Mass Spectrometry", *Anal. Chem.*, 1994, 66, 3858–3863.

Berson et al., "General Principles of Radioimmunoassay", *Clin. Chim. Acta*, 1968, 22, 51–60.

Bruce et al., "Bio–Affinity Characterization Mass Spectrometry", *Rapid Commun. Mass Spectrom.*, 1995, 9, 644–650.

Bruins et al., "Ion Spray Interface for Combined Liquid Chromatography/Atmospheric Pressure Ionization Mass Spectrometry", *Anal. Chem.*, 1987, 59, 2642–2646.

Busman et al., "Observation of Large Multimers in the Electrospray Ionization Mass Spectrometry of Peptides", *Rapid Commun. Mass Spectrom.*, 1994, 8, 211–216.

Cai et al., "Capillary electrohoresis—mass spectrometry",*J. Chromatogr.*, 1995, 703, 667–692.

(List continued on next page.)

*Primary Examiner*—Stephanie Zitomer
(74) *Attorney, Agent, or Firm*—Woodcock Washburn LLP

(57) ABSTRACT

The present invention provides methods for the determination of the structure of biomolecular targets, as well as the site and nature of the interaction between ligands and biomolecular targets. The present invention also provides methods for the determination of the relative affinity of a ligand for the biomolecular target it interacts with. Also provided are methods for screening ligand or combinatorial libraries of compounds against one or more than one biological target molecules. The methods of the invention also allow determination of the relative binding affinity of combinatorial and other compounds for a biomolecular target. The present invention further provides methods for the use of mass modifying tags for screening multiple biomolecular targets. In a preferred embodiment, ligands which have great specificity and affinity for molecular interaction sites on biomolecules, especially RNA can be identified. In preferred embodiments, such identification can be made simultaneously with libraries of ligands.

16 Claims, 15 Drawing Sheets

OTHER PUBLICATIONS

Cheng et al., "Using Electrospray Ionization FTICR Mass Spectrometry to Study Competitive Binding of Inhibitors to Carbonic Anhydrase", *J. Am. Chem. Soc.*, 1995, 117, 8859–8860.

Chu et al., "Affinity Capillary Electrophoresis", *Acc. Chem. Res.*, 1995, 28, 461–468.

Chu et al., "Using Affinity Capillary Electrophoresis to Identify the Peptide in a Peptide Library that Binds Most Tightly to Vancomycin", *J. Org. Chem.*, 1993, 58, 648–652.

Chu et al., "Affinity Capillary Electrophoresis—Mass Spectrometry for Screening Combinatorial Libraries", *J. Am. Chem. Soc.*, 1996, 118, 7827–7835.

Cohen et al., "Probing the solution structure of the DNA–binding protein Max by a combination of proteolysis and mass spectrometry", *Protein Sci.*, 1995, 4, 1088–1099.

Doctycz et al., "Accumulation and Storage of Ionized Duplex DNA Molecules in a Quadrupole Ion Trap", *Anal. Chem.*, 1994, 66, 3416–3422.

Dunayevskiy et al., "Mass Spectrometric Identification of Ligands Selected from Combinatorial Libraries Using Gel Filtration", *Rapid Commun. Mass Spectrom.*, 1997, 11, 1178–1184.

Ecker et al., "Combinatorial Drug Discovery: Which Methods Will Produce the Greatest Value", *Biotech.*, 1995, 13, 351–360.

Erickson et al., "Macromolecular X–Ray Crystallography and NMR as Tools for Structure–based Drug Design", *Ann. Rep. Med. Chem.*, 1992, vol. 27, Ch. 29, 271–289.

Feng et al., "Analysis of Antibodies and Other Large Glycoproteins in the Mass Range of 150 000–200 000 Da by Electrospray Ionization Mass Spectrometry", *Anal. Chem.*, 1992, 64, 2090–2095.

Gale et al., "Observation of Duplex DNA–Drug Noncovalent Complexes by Electrospray Ionization Mass Spectrometry", *J. Am. Chem. Soc.*, 1994, 116, 6027–6028.

Ganem et al., "Detecting Noncovalent Complexes of Biological Macromolecules: New Applications of Ion–Spray Mass Spectrometry", *ChemTracts–Org. Chem.*, 1993, 6, 1–22.

Ganem et al., "Detection of Oligonucleotide Duplex Forms by Ion–Spray Mass Spectrometry", *Tetra. Lett.*, 1993, 34(9), 1445–1448.

Gao et al., "Screening Derivatized Peptide Libraries for Tight Binding Inhibitors to Carbonic Anhydrase II by Electrospray Ionization–Mass Spectrometry", *J. Med. Chem.*, 1996, 39, 1949–1955.

Glover et al., "Sequencing of Oligonucleotides Using High Performance Liquid Chromatography and Electrospray Mass Spectrometry", *Rapid Commun. Mass Spectrom.*, 1995, 9, 897–901.

Goodlett et al., "Direct Observation of a DNA Quadruplex by Electrospray Ionization Mass Spectrometry", *Biol. Mass Spectrom.*, 1993, 22, 181–183.

Greig et al., "Measurement of Macromolecular Binding Using Electrospray Mass Spectrometry. Determination of Dissocation Constants for Oligonucleotide—Serum Albumin Complexes", *J. Am. Chem. Soc.*, 1995, 117, 10765–10766.

Henion et al., "Mass Spectrometric Investigations of Drug–Receptor Interactions", *Ther. Drug Monitoring*, 1993, 15(6), 563–569.

Hillenkamp et al., "Matrix–Assisted Laser Desorption/Ionization Mass Spectrometry of Bipolymers", *Anal. Chem.*, 1991, 63(24), 1193A–1202A.

Hu et al., "Determining Calcium–binding Stoichiometry and Cooperativity of Parvalbumin and Calmodulin by Mass Spectrometry", *J. Mass Spectrom.*, 1995, 30, 1076–1079.

Huang et al., "Packed–Capillary Liquid Chromatography/Ion–Spray Tandem Mass Spectrometry Determination of Biomolecules", *Anal. Chem.*, 1991, 63, 732–739.

Huang et al., "LC/MS and LC/MS/MS Determination of Protein Tryptic Digests", *J. Am. Soc. Mass Spectrom.*, 1990, 1(2), 158–165.

Jefson, "Applications of NMR Spectroscopy to Protein Structure Determination", *Ann. Rep. Med. Chem.*, 1998, vol. 23, Ch. 28, 275–283.

Jensen et al., "Mass Spectrometric Characterization of UV–Crosslinked Protein–Nucleic Acid Complexes", *42nd ASMS Conf. On Mass Spectrom. and Allied Topics*, 1994, 923.

Jensen et al., "Direct Observation of UV–crosslinked Protein–Nucleic Acid Complexes by Matrix–assisted Laser Desorption Ionization Mass Spectrometry", *Rapid Commun. Mass Spectrom.*, 1993, 7, 496–501.

Jonsson et al., "Real–Time Biospecific Interaction Analysis Using Surface Plasmon Resonance and a Sensor Chip Technology", *Biotech.*, 1991, 11(5), 620–627.

Karlsson et al., "Kinetic analysis of monoclonal antibody––antigen interactions with a new biosensor based analytical system", *J. Immunol. Methods*, 1991, 145, 229–240.

Kassel et al., "Direct Coupling of an Automated 2–Dimenstional Microcolumn Affinity Chromatography–Capillary HPLC System with Mass Spectrometry for Biomolecular Analysis", in *Techniques in Protein Chemistry*, J.Crabb (ed.), Academic Press, San Diego, 1995, Ch, VI, 39–46.

Knight et al., "Electrospray Ionization Mass Spectrometry as a Mechanistic Tool: Mass of Human Leucocyte Elastase and a β–Lactam–Derived E–1 Complex", *Biochem.*, 1993, 32, 2031–2035.

Lane et al., "SPARC Is a Source of Copper–binding Peptides that Stimulate Angiogenesis", *J. Cell Biol.*, 1994, 125(4), 929–943.

Li et al., "Mass Spectrometric Studies on Noncovalent Dimers of Leucine Zipper Peptides", *J. Am. Chem. Soc.*, 1993, 115, 8409–8413.

Light–Wahl et al., "Observation of a Small Oligonucleotide Duplex by Electrospray Ionization Mass Spectrometry", *J. Am. Chem. Soc.*, 1993, 115, 803–804.

Light–Wahl et al., "Observation of the Noncovalent Quaternary Associations of Proteins by Electrospray Ionization Mass Spectrometry", *J. Am. Chem. Soc.*, 1994, 116, 5271–5278.

Light–Wahl et al., "Collisionally Activated Dissociation and Tandem Mass Spectrometry of Intact Hemoglobin β–Chain Variant Proteins with Electrospray Ionization", *Biol. Mass Spectrom.*, 1993, 22, 112–120.

Lim et al., "Recognition of Cell–wall Peptide Ligands by Vancomycin Group Antibiotics: Studies Using Ion Spray Mass Spectrometry", *J. Mass Spectrom.*, 1995, 30, 708–714.

Little et al., "Rapid Sequencing of Oligonucleotides by High–Resolution Mass Spectrometry", *J. Am. Chem. Soc.*, 1994, 116, 4893–4897.

Little et al., "Sequencing 50–mer DNAs Using Electrospray Tandem Mass Spectrometry and Complementary Fragmentation Methods", *J. Am. Chem. Soc.*, 1995, 117, 6783–6784.

Little et al., "Infrared Multiphoton Dissociation of Large Multiply Charged Ions for Biomolecule Sequencing", *Anal. Chem.*, 1994, 66, 2809–2815.

Little et al., "Verification of 50–to 100–mer DNA and RNA sequences with high–resolution mass spectrometry", *Proc. Natl. Acad. Sci. USA*, 1995, 92, 2318–2322.

Loo, "Bioanalytical Mass Spectrometry: Many Flavors to Choose", *Bioconjugate Chem.*, 1995, 6, 644–665.

Loo, "Observation of Large Subunit Protein Complexes by Electrospray Ionization Mass Spectrometry", *J. Mass Spectrom.*, 1995, 30, 180–183.

Loo et al., "Use of Electrospray Ionization Mass Spectrometry to Probe Antisense Peptide Interactions", *Biol. Mass Spectrom.*, 1994, 23, 6–12.

Loo et al., "Interactions of Angiotensin Peptides and Zinc Metal Ions Probed by Electrospray Ioniztion Mass Spectrometry", *J. Am. Soc. Mass Spectrom.*, 1994, 5(11), 959–965.

Marshall et al., "Fouriere Transform Ion Cyclotron Resonance Mass Spectrometry: The Teenage Years", *Anal. Chem.*, 1991, 63(4), A215–A229.

McLuckey et al., "Tandem Mass Spectrometry of Small, Multiply Charged Oligonucleotides", *J. Am. Soc. Mass Spectrom.*, 1992, 3(1), 60–70.

McLuckey et al., "Decompositions of Multiply Charged Oligonucleotide Anions", *J. Am. Chem. Soc.*, 1993, 115, 12085–12095.

Nelson et al., "Mass Determination of Human Immunoglobulin IgM Using Matrix–assisted Laser Desorption/Ionization Time–of–flight Mass Spectrometry", *Rapid Commun. Mass Spectrom.*, 1994, 8, 627–631.

Ni et al., "Interpretation of Oligonucleotide Mass Spectra for Determinationof Sequence Using Electrospray Ionization and Tandem Mass Spectrometry", *Anal. Chem.*, 1996, 68, 1989–1999.

Nordhoff et al., "Direct Mass Spectrometric Sequencing of Low–picomole Amounts of Oligodeoxynucleotides with up to 21 Bases by Matrix–assisted Laser Desorption/Ionization Mass Spectrometry", *J. Mass Spectrom.*, 1995, 30, 99–112.

Pieles et al., "Matrix–assisted laser desorption ionization time–of–flight mass spectrometry: a powerful tool for the mass and sequence analyis of natural and modified oligonucleotides", *Nucl. Acid Res.*, 1993, 21(14), 3191–3196.

Rossomando et al., "Identification of Tyr–185 as the site of tyrosine autophosphorylation of recombinant mitogen–activated protein kinase p42$^{mapk}$", *Proc. Natl. Acad. Sci USA*, 1992, 89, 5779–5783.

Shaler et al., "Analysis of Enzymatic DNA Sequencing Reactions by Matrix–assisted Laser Desorption/Ionization Time–of–flight Mass Spectrometry", *Rapid Commun. Mass Spectrom.*, 1995, 9, 942–947.

Smith et al., "The Observation of Non–covalent Interactions in Solution by Electrospray Ionization Mass Spectrometry: Promise, Pitfalls and Prognosis", *J. Biol. Mass Spectrom.*, 1993, 22, 493–501.

Smith et al., "New Developments in Biochemical Mass Spectrometry: Electrospray Ionization", *Anal. Chem.*, 1990, 62, 882–899.

Sternberg et al., "Display of peptides and proteins on the surface of bacteriophage γ", *Proc. Natl. Acad. Sci. USA*, 1995, 92, 1609–1613.

Udenfriend et al., "Scintillation Proximity Assay: A Sensitive and Continuous Isotopic Method for Monitoring Ligand/Receptor and Antigen/Antibody Interactions", *Anal. Biochem.*, 1987, 161, 494–500.

Winger et al., "High–Resolution Accurate Mass Measurements of Biomolecules Using a New Electrospray Ionization Ion Cyclotron Resonance Mass Spectrometer", *J. Am. Soc. Mass Spectrom.*, 1993, 4(7), 566–577.

Witkowska et al., "Mass Spectrometric Analysis of a Native Zinc–Finger Structure: The Glucocorticoid Receptor DNA Binding Domain", *J. Am. Chem. Soc.*, 1995, 117(12), 3319–3324.

Cheng et al., "Electrospray Ionization with High Performance Fourier Transform Ion Cyclotron Resonance Mass Spectrometry for the Study of Noncovalent Biomolecular Complexes", in *Techniques in Protein Chemistry*, 1996, vol. 7, 13–21.

\* cited by examiner

16S A Site rRNA

```
              U    U
5'- GGCGUCA CACC   C
    CCGCUGA GUGG   G
              A
```

Control RNA

```
              U    U
5'- GGCGUCACACC    C
    CCGCAG UGUGG   G
              A
```

Figure 1. Sequence and structure of 27mer RNA target

Figure 8. MS Fragmentation of DNA:DNA duplexes

Figure 9. MS Fragmentation of DNA:RNA duplexes

MASS SPECTROMETRIC METHODS FOR BIOMOLECULAR SCREENING

This application claims benefit of Provisional Application No. 60/076,534 filed Mar. 2, 1998.

FIELD OF THE INVENTION

The present invention is directed to methods for the use of mass spectrometry for the determination of the structure of a biomolecule especially a nucleic acid target, the site(s) of interaction between ligands and the target, the relative binding affinity of ligands for the target and other useful information. The present invention also provides methods for the use of mass spectrometry for screening chemical mixtures or libraries, especially combinatorial libraries, for individual compounds that bind to a selected target and can be used in pharmaceuticals, veterinary drugs, agricultural chemicals industrial chemicals and otherwise. The present invention is further directed to methods for screening multiple targets simultaneously against, e.g. a combinatorial library of compounds.

A further aspect of the invention provides methods for determining the interaction between one or a plurality of molecular species, especially "small" molecules and a molecular interaction site on a nucleic acid, especially an RNA.

BACKGROUND OF THE INVENTION

The process of drug discovery is changing at a fast pace because of the rapid progress and evolution of a number of technologies that impact this process. Drug discovery has evolved from what was, several decades ago, essentially random screening of natural products, into a scientific process that not only includes the rational and combinatorial design of large numbers of synthetic molecules as potential bioactive agents, such as ligands, agonists, antagonists, and inhibitors, but also the identification, and mechanistic and structural characterization of their biological targets, which may be polypeptides, proteins, or nucleic acids. These key areas of drug design and structural biology are of tremendous importance to the understanding and treatment of disease. However, significant hurdles need to be overcome when trying to identify or develop high affinity ligands for a particular biological target. These include the difficulty surrounding the task of elucidating the structure of targets and targets to which other molecules may be bound or associated, the large numbers of compounds that need to be screened in order to generate new leads or to optimize existing leads, the need to dissect structural similarities and dissimilarities between these large numbers of compounds, correlating structural features to activity and binding affinity, and the fact that small structural changes can lead to large effects on biological activities of compounds.

Traditionally, drug discovery and optimization have involved the expensive and time-consuming, and therefore slow, process of synthesis and evaluation of single compounds bearing incremental structural changes. When using natural products, the individual components of extracts had to be painstakingly separated into pure constituent compounds prior to biological evaluation. Further, all compounds had to be carefully analyzed and characterized prior to in vitro screening. These screens typically included evaluation of candidate compounds for binding affinity to their target, competition for the ligand binding site, or efficacy at the target as determined via inhibition, cell proliferation, activation or antagonism end points. Considering all these facets of drug design and screening that slow the process of drug discovery, a number of approaches to alleviate or remedy these matters, have been implemented by those involved in discovery efforts.

One way in which the drug discovery process is being accelerated is by the generation of large collections, libraries, or arrays of compounds. The strategy of discovery has moved from selection of drug leads from among compounds that are individually synthesized and tested to the screening of large collections of compounds. These collections may be from natural sources (Sternberg et al., Proc. Natl. Acad. Sci. USA, 1995, 92, 1609–1613) or generated by synthetic methods such as combinatorial chemistry (Ecker and Crooke, Bio/Technology, 1995, 13, 351–360 and U.S. Pat. No. 5,571,902, incorporated herein by reference). These collections of compounds may be generated as libraries of individual, well-characterized compounds synthesized, e.g. via high throughput, parallel synthesis or as a mixture or a pool of up to several hundred or even several thousand molecules synthesized by split-mix or other combinatorial methods. Screening of such combinatorial libraries has usually involved a binding assay to determine the extent of ligand-receptor interaction (Chu et al., J. Am. Chem. Soc., 1996, 118, 7827–35). Often the ligand or the target receptor is immobilized onto a surface such as a polymer bead or plate. Following detection of a binding event, the ligand is released and identified. However, solid phase screening assays can be rendered difficult by non-specific interactions.

Whether screening of combinatorial libraries is performed via solid-phase, solution methods or otherwise, it can be a challenge to identify those components of the library that bind to the target in a rapid and effective manner and which, hence, are of greatest interest. This is a process that needs to be improved to achieve ease and effectiveness in combinatorial and other drug discovery processes. Several approaches to facilitating the understanding of the structure of biopolymeric and other therapeutic targets have also been developed so as to accelerate the process of drug discovery and development. These include the sequencing of proteins and nucleic acids (Smith, in Protein Sequencing Protocols, Humana Press, Totowa, N.J., 1997; Findlay and Geisow, in Protein Sequencing: A Practical Approach, IRL Press, Oxford, 1989; Brown, in DNA Sequencing, IRL Oxford University Press, Oxford, 1994; Adams, Fields and Venter, in Automated DNA Sequencing and Analysis, Academic Press, San Diego, 1994). These also include elucidating the secondary and tertiary structures of such biopolymers via NMR (Jefson, Ann. Rep. in Med. Chem., 1988, 23, 275; Erikson and Fesik, Ann. Rep. in Med. Chem., 1992, 27, 271–289), X-ray crystallography (Erikson and Fesik, Ann. Rep. in Med. Chem., 1992, 27, 271–289) and the use of computer algorithms to attempt the prediction of protein folding (Copeland, in Methods of Protein Analysis: A Practical Guide to Laboratory Protocols, Chapman and Hall, New York, 1994; Creighton, in Protein Folding, W. H. Freeman and Co., 1992). Experiments such as ELISA (Kemeny and Challacombe, in ELISA and other Solid Phase Immunoassays: Theoretical and Practical Aspects; Wiley, New York, 1988) and radioligand binding assays (Berson and Yalow, Clin. Chim. Acta, 1968, 22, 51–60; Chard, in "An Introduction to Radioimmunoassay and Related Techniques," Elsevier press, Amsterdam/New York, 1982), the use of surface-plasmon resonance (Karlsson, Michaelsson and Mattson, J. Immunol. Methods, 1991, 145, 229; Jonsson et al., Biotechniques, 1991, 11, 620), and scintillation proximity assays (Udenfriend, Gerber and Nelson, Anal. Biochem., 1987, 161, 494–500) are being used to understand the nature of the receptor-ligand interaction.

All of the foregoing paradigms and techniques are now available to persons of ordinary skill in the art and their understanding and mastery is assumed herein.

Likewise, advances have occurred in the chemical synthesis of compounds for high-throughput biological screening. Combinatorial chemistry, computational chemistry, and the synthesis of large collections of mixtures of compounds or of individual compounds have all facilitated the rapid synthesis of large numbers of compounds for in vitro screening. Despite these advances, the process of drug discovery and optimization entails a sequence of difficult steps. This process can also be an expensive one because of the costs involved at each stage and the need to screen large numbers of individual compounds. Moreover, the structural features of target receptors can be elusive.

One step in the identification of bioactive compounds involves the determination of binding affinity of test compounds for a desired biopolymeric or other receptor, such as a specific protein or nucleic acid or combination thereof. For combinatorial chemistry, with its ability to synthesize, or isolate from natural sources, large numbers of compounds for in vitro biological screening, this challenge is magnified. Since combinatorial chemistry generates large numbers of compounds or natural products, often isolated as mixtures, there is a need for methods which allow rapid determination of those members of the library or mixture that are most active or which bind with the highest affinity to a receptor target.

From a related perspective, there are available to the drug discovery scientist a number of tools and techniques for the structural elucidation of biologically interesting targets, for the determination of the strength and stoichiometry of target-ligand interactions, and for the determination of active components of combinatorial mixtures.

Techniques and instrumentation are available for the sequencing of biological targets such as proteins and nucleic acids (e.g. Smith, in Protein Sequencing Protocols, 1997 and Findlay and Geisow, in Protein Sequencing: A Practical Approach, 1989) cited previously. While these techniques are useful, there are some classes and structures of biopolymeric target that are not susceptible to such sequencing efforts, and, in any event, greater convenience and economy have been sought. Another drawback of present sequencing techniques is their inability to reveal anything more than the primary structure, or sequence, of the target.

While X-ray crystallography is a very powerful technique that can allow for the determination of some secondary and tertiary structure of biopolymeric targets (Erikson and Fesik, Ann. Rep. in Med. Chem., 1992, 27, 271–289), this technique can be an expensive procedure and very difficult to accomplish. Crystallization of biopolymers is extremely challenging, difficult to perform at adequate resolution, and is often considered to be as much an art as a science. Further confounding the utility of X-ray crystal structures in the drug discovery process is the inability of crystallography to reveal insights into the solution-phase, and therefore the biologically relevant, structures of the targets of interest.

Some analysis of the nature and strength of interaction between a ligand (agonist, antagonist, or inhibitor) and its target can be performed by ELISA (Kemeny and Challacombe, in ELISA and other Solid Phase Immunoassays: 1988), radioligand binding assays (Berson and Yalow, Clin. 1968, Chard, in "An Introduction to Radioimmunoassay and Related Techniques," 1982), surface-plasmon resonance (Karlsson, Michaelsson and Mattson, 1991, Jonsson et al., Biotechniques, 1991), or scintillation proximity assays (Udenfriend, Gerber and Nelson, Anal. Biochem., 1987), all cited previously. The radioligand binding assays are typically useful only when assessing the competitive binding of the unknown at the biding site for that of the radioligand and also require the use of radioactivity. The surface-plasmon resonance technique is more straightforward to use, but is also quite costly. Conventional biochemical assays of binding kinetics, and dissociation and association constants are also helpful in elucidating the nature of the target-ligand interactions.

When screening combinatorial mixtures of compounds, the drug discovery scientist will conventionally identify an active pool, deconvolute it into its individual members via resynthesis, and identify the active members via analysis of the discrete compounds. Current techniques and protocols for the study of combinatorial libraries against a variety of biologically relevant targets have many shortcomings. The tedious nature, high cost, multi-step character, and low sensitivity of many of the above-mentioned screening technologies are shortcomings of the currently available tools. Further, available techniques do not always afford the most relevant structural information—the structure of a target in solution, for example. Instead they provide insights into target structures that may only exist in the solid phase. Also, the need for customized reagents and experiments for specific tasks is a challenge for the practice of current drug discovery and screening technologies. Current methods also fail to provide a convenient solution to the need for deconvolution and identification of active members of libraries without having to perform tedious re-syntheses and re-analyses of discrete members of pools or mixtures.

Therefore, methods for the screening and identification of complex chemical libraries especially combinatorial libraries are greatly needed such that one or more of the structures of both the target and ligand, the site of interaction between the target and ligand, and the strength of the target-ligand interaction can be determined. Further, in order to accelerate drug discovery, new methods of screening combinatorial libraries are needed to provide ways for the direct identification of the bioactive members from a mixture and to allow for the screening of multiple biomolecular targets in a single procedure. Straightforward methods that allow selective and controlled cleavage of biopolymers, while also analyzing the various fragments to provide structural information, would be of significant value to those involved in biochemistry and drug discovery and have long been desired. Also, it is preferred that the methods not be restricted to one type of biomolecular target, but instead be applicable to a variety of targets such as nucleic acids, peptides, proteins and oligosaccharides.

OBJECTS OF THE INVENTION

A principal object of the present invention is to provide novel methods for the determination of the structure of biomolecular targets and ligands that interact with them and to ascertain the nature and sites of such interactions.

A further object of the invention is to determine the structural features of biomolecular targets such as peptides, proteins, oligonucleotides, and nucleic acids such as the primary sequence, the secondary and folded structures of biopolymers, and higher order tertiary and quaternary structures of biomolecules that result from intramolecular and intermolecular interactions.

Yet another object of the invention is to determine the site(s) and nature of interaction between a biomolecular target and a binding ligand or ligands. The binding ligand may be a "small" molecule, a biomolecule such as a peptide, oligonucleotide or oligosaccharide, a natural product, or a member of a combinatorial library.

A further object of the invention is to determine the relative binding affinity or dissociation constant of ligands that bind to biopolymer targets. Preferably, this gives rise to a determination of relative binding affinities between a biopolymer such as an RNA/DNA target and ligands e.g. members of combinatorially synthesized libraries.

A still further object of the present invention is to provide a general method for the screening of combinatorial libraries comprising individual compounds or mixtures of compounds against a biomolecular target such as a nucleic acid, so as to determine which components of the library bind to the target.

An additional object of the present invention is to provide methods for the determination of the molecular weight and structure of those members of a combinatorial library that bind to a biomolecular target.

Yet another object of the invention is to provide methods for screening multiple targets such as nucleic acids, proteins, and other biomolecules and oligomers simultaneously against a combinatorial library of compounds.

A still further object of the invention is to ascertain the specificity and affinity of compounds, especially "small" organic molecules to bind to or interact with molecular interaction sites of biological molecules, especially nucleic acids such as RNA. Such molecules may be and preferably do form ranked hierarchies of ligands and potential ligands for the molecular interaction sites, ranked in accordance with predicted or calculated likelihood of interaction with such sites.

Another object of the present invention is to alleviate the problem of peak overlap in mass spectra generated from the analysis of mixtures of screening targets and combinatorial or other mixtures of compounds. In a preferred embodiment, the invention provides methods to solve the problems of mass redundancy in combinatorial or other mixtures of compounds, and also provides methods to solve the problem of mass redundancy in the mixture of targets being screened.

A further object of the invention is to provide methods for determining the binding specificity of a ligand for a target in comparison to a control. The present invention facilitates the determination of selectivity, the identification of non-specific effects and the elimination of non-specific ligands from further consideration for drug discovery efforts.

The present invention provides, inter alia, a series of new methods and applications for the determination of the structure and nature of binding of ligands to a wide variety of biomolecular targets. This new approach provides structural information for screening combinatorial libraries for drug lead discovery.

SUMMARY OF THE INVENTION

One aspect of the invention is a method to determine the structure of biomolecular targets such as nucleic acids using mass spectrometry. The method provides not only the primary, sequence structure of nucleic acid targets, but also information about the secondary and tertiary structure of nucleic acids, RNA and DNA, including mismatched base pairs, loops, bulges, kinks, and stem structures. This can be accomplished in accordance with one embodiment by incorporating deoxynucleotide residues or other modified residues into an oligoribonucleotide at specific sites followed by selective cleavage of these hybrid RNA/DNA nucleic acids in a mass spectrometer. It has now been found that electrospray ionization of the nucleic acid, cleavage of the nucleic acid, and subsequent tandem $MS^n$ spectrometry affords a pattern of fragments that is indicative of the nucleic acid sequence and structure. Cleavage is dependent on the sites of incorporation of the deoxynucleotide or other foreign residues and the secondary structure of the nucleic acid. This method therefore provides mass spectral data that identifies the sites and types of secondary structure present in the sequence of nucleic acids.

When the present methods are performed on a mixture of the biomolecular target and a ligand or molecule that binds to the target, it is possible to ascertain both the extent of interaction and the location of this interaction between ligand and biomolecule. The binding of the ligand to the biomolecule protects the binding site on the biomolecule from facile cleavage during mass spectrometry. Therefore, comparison of ESI-$MS^n$ mass spectra generated, using this method, for RNA/DNA in the presence and the absence of a binding ligand or drug reveals the location of binding. This altered cleavage pattern is clearly discerned in the mass spectrum and correlated to the sequence and structure of the nucleic acid. Comparison of the abundance of the nucleic acid-ligand noncovalent complex ion to the abundance of a similar complex ion generated from a standard compound (such as paromomycin for the 16S RNA A site ) whose binding affinity is known, allows for the determination of relative binding affinity of the test ligand.

The methods of this invention can be used for the rapid screening of large collections of compounds. It is also possible to screen mixtures of large numbers of compounds that are generated via combinatorial or other means. When a large mixture of compounds is exposed to a biomolecular target, such as a nucleic acid, a small fraction of ligands may exhibit some binding affinity to the nucleic acid. The actual number of ligands that may be detected as binders is based on the concentration of the nucleic acid target, the relative concentrations of the components of the combinatorial mixture, and the relative binding affinities of these components. The method is capable of separating different noncovalent complexes, using techniques such as selective ion trapping, or accumulation and analyzing each complex for the structure and identity of the bound ligand using collisionally activated dissociation or $MS^n$ experiments. The methods of this invention, therefore, can not only serve as methods to screen combinatorial libraries for molecules that bind to biomolecular targets, but can also provide, in a straightforward manner, the structural identity of the bound ligands. In this manner, any mass redundancy in the combinatorial library does not pose a problem, as the methods can provide high resolution molecular masses and also able to discern differences between the different structures of ligands of identical molecular mass using tandem methods.

In accordance with preferred embodiments, a target biomolecule such as an RNA having a molecular interaction site, is presented with one or more ligands or suspected ligands for the interaction site under conditions such that interaction or binding of the ligand to the molecular interaction site can occur. The resulting complex, which may be of one or even hundreds of individual complexes of ligands with the RNA or other biomolecule, is then subjected to mass spectrometric evaluation in accordance with the invention. "Preparative" mass spectrometry can isolate individual complexes which can then be fragmented under controlled conditions within the mass spectrometric environment for subsequent analysis. In this way, the nature and degree of binding of the ligands to the molecular interaction site can be ascertained. Identification of specific, strong binding ligands can be made and those selected for use either as therapeutics, agricultural, industrial or other chemicals, or the same used as lead compounds for subsequent modification into improved forms for such uses.

A further application of the present invention is the use of mass spectrometric methods for the simultaneous screening of multiple biomolecular targets against combinatorial libraries or mixtures of compounds. This rather complex screening procedure is made possible by the combined power of the mass spectrometric methods used and the way in which the screening is performed. When screening multiple target nucleic acids, for example, mass redundancy is a concern, especially if two or more targets are of similar sequence composition or mass. This problem is alleviated by the present invention, by using special mass modifying, molecular weight tags on the different nucleic acid targets being studied. These mass modifying tags are typically large molecular weight, non-ionic polymers including but not limited to, polyethylene glycols, polyacrylamides and dextrans, that are available in many different sizes and weights, and which may be attached at one or more of many different possible sites on nucleic acids. Thus similar nucleic acid targets may be differentially tagged and now be readily differentiated, in the mass spectrum, from one another by their distinctly different mass to charge ratios (m/z signals). Using the methods of this invention, screening efforts can be significantly accelerated because multiple targets can now be screened simultaneously against mixtures of large numbers of compounds.

Another related advantage of the methods of this invention is the ability to determine the specificity of binding interactions between a new ligand and a biomolecular target. By simultaneously screening a target nucleic acid, for example, and one or more control nucleic acids against a combinatorial library or a specific ligand, it is possible to ascertain, using the methods of this invention, whether the ligand binds specifically to only the target nucleic acids, or whether the binding observed with the target is reproduced with control nucleic acids and is therefore non-specific.

The methods of the invention are applicable to the study of a wide variety of biomolecular targets that include, but are not limited to, peptides, proteins, receptors, antibodies, oligonucleotides, RNA, DNA, RNA/DNA hybrids, nucleic acids, oligosaccharides, carbohydrates, and glycopeptides. The molecules that may be screened by using the methods of this invention include, but are not limited to, organic or inorganic, small to large molecular weight individual compounds, mixtures and combinatorial libraries of ligands, inhibitors, agonists, antagonists, substrates, and biopolymers, such as peptides, nucleic acids or oligonucleotides. The mass spectrometric techniques which can be used in the methods of the invention include, but are not limited to, $MS^n$, collisionally activated dissociation (CAD) and collisionally induced dissociation (CID) and infrared multiphoton dissociation (IRMPD). A variety of ionization techniques may be used including, but not limited to, electrospray, MALDI and FAB. The mass detectors used in the methods of this invention include, but are not limited to, FTICR, ion trap, quadrupole, magnetic sector, time of flight (TOF), Q-TOF, and triple quadrupole. The methods of this invention may also use "hyphenated" techniques such as, but not limited to, LC/MS and CE/MS, all as described more fully hereinafter.

BRIEF DESCRIPTION OF THE DRAWINGS

FIG. 1 shows the sequence and structure of the 27-mer RNA target corresponding to the 16S rRNA A-site.

SUMMARY OF EXEMPLARY MASS SPECTROMETRIC TECHNIQUES

Figure 2A:
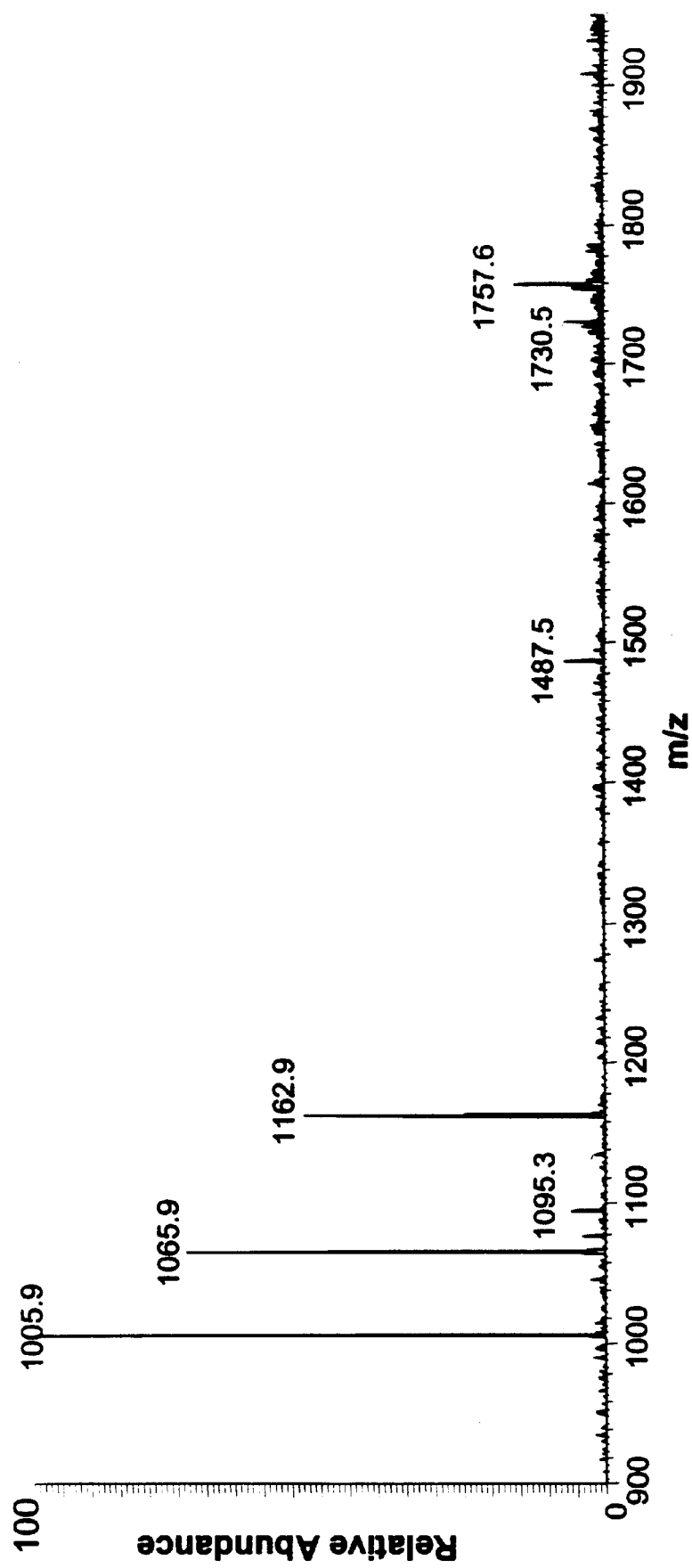
FIGS. 2A and 2B show the ESI-CID-MS of a 27-mer RNA/DNA hybrid in the presence and absence of paromomycin.

Mass spectrometry (MS) is a powerful analytical tool for the study of molecular structure and interaction between small and large molecules. The current state-of-the-art in MS is such that less than femtomole quantities of material can be readily analyzed using mass spectrometry to afford information about the molecular contents of the sample. An accurate assessment of the molecular weight of the material may be quickly obtained, irrespective of whether the sample's molecular weight is several hundred, or in excess of a hundred thousand, atomic mass units or Daltons (Da). It has now been found that mass spectrometry can elucidate significant aspects of important biological molecules. One reason for the utility of MS as an analytical tool in accordance with the invention is the availability of a variety of different MS methods, instruments, and techniques which can provide different pieces of information about the samples.

One such MS technique is electrospray ionization mass spectrometry (ESI-MS) (Smith et al., Anal. Chem., 1990, 62, 882–899; Snyder, in Biochemical and biotechnological applications of electrospray ionization mass, American Chemical Society, Washington, DC, 1996; Cole, in Electrospray ionization mass spectrometry: fundamentals, instrumentation, Wiley, New York, 1997). ESI produces highly charged droplets of the sample being studied by gently nebulizing the sample solution in the presence of a very strong electrostatic field. This results in the generation of highly charged droplets that shrink due to evaporation of the neutral solvent and ultimately lead to a "Coulombic explosion" that affords multiply charged ions of the sample material, typically via proton addition or abstraction, under mild conditions. ESI-MS is particularly useful for very high molecular weight biopolymers such as proteins and nucleic acids greater than 10 kDa in mass, for it affords a distribution of multiply-charged molecules of the sample biopolymer without causing any significant amount of fragmentation.

The fact that several peaks are observed from one sample, due to the formation of ions with different charges, contributes to the accuracy of ESI-MS when determining the molecular weight of the biopolymer because each observed peak provides an independent means for calculation of the molecular weight of the sample. Averaging the multiple readings of molecular weight so obtained from a single ESI-mass spectrum affords an estimate of molecular weight that is much more precise than would be obtained if a single molecular ion peak were to be provided by the mass spectrometer. Further adding to the flexibility of ESI-MS is the capability to obtain measurements in either the positive or negative ionization modes.

Matrix-Assisted Laser Desorption/Ionization Mass Spectrometry (MALDI-MS) is another method that can be used for studying biomolecules (Hillenkamp et al., Anal. Chem., 1991, 63, 1193A–1203A). This technique ionizes high molecular weight biopolymers with minimal concomitant fragmentation of the sample material. This is typically accomplished via the incorporation of the sample to be analyzed into a matrix that absorbs radiation from an incident UV or IR laser. This energy is then transferred from the matrix to the sample resulting in desorption of the sample into the gas phase with subsequent ionization and minimal fragmentation. One of the advantages of MALDI-MS over ESI-MS is the simplicity of the spectra obtained as MALDI spectra are generally dominated by singly charged species. Typically, the detection of the gaseous ions generated by MALDI techniques, are detected and analyzed by determining the time-of-flight (TO) of these ions. While MALDI-TOF MS is not a high resolution technique, resolution can be improved by making modifications to such systems, by the use of tandem MS techniques, or by the use of other types of analyzers, such as Fourier transform (FT) and quadrupole ion traps.

Fourier transform mass spectrometry (FTMS) is an especially useful analytical technique because of its ability to make mass measurements with a combination of accuracy and resolution that is superior to other MS detection techniques, in connection with ESI or MALDI ionization (Amster, J. Mass Spectrom., 1996, 31, 1325–1337). Further it may be used to obtain high resolution mass spectra of ions generated by any of the other ionization techniques. The basis for FTMS is ion cyclotron motion, which is the result of the interaction of an ion with a unidirectional magnetic field. The mass-to-charge ratio of an ion (m/q or m/z) is determined by a FTMS instrument by measuring the cyclotron frequency of the ion. The insensitivity of the cyclotron frequency to the kinetic energy of an ion is one of the fundamental reasons for the very high resolution achievable with FTMS. FTMS is an excellent detector in conventional or tandem mass spectrometry, for the analysis of ions generated by a variety of different ionization methods including ESI and MALDI, or product ions resulting from collisionally activated dissociation (CAD).

Collisionally activated dissociation (CAD), also known as collision induced dissociation (CID), is a method by which analyte ions are dissociated by energetic collisions with neutral or charged species, resulting in fragment ions which can be subsequently mass analyzed. Mass analysis of fragment ions from a selected parent ion can provide certain sequence or other structural information relating to the parent ion. Such methods are generally referred to as tandem mass spectrometry (MS or MS/MS) methods and are the basis of the some of MS based biomolecular sequencing schemes being employed today.

FTICR-MS, like ion trap and quadrupole mass analyzers, allows selection of an ion that may actually be a weak non-covalent complex of a large biomolecule with another molecule (Marshall and Grosshans, Anal. Chem., 1991, 63, A215–A229; Beu et al., J. Am. Soc. Mass Spectrom., 1993, 4, 566–577; Winger et al., J. Am. Soc. Mass Spectrom., 1993, 4, 566–577); (Huang and Henion, Anal. Chem., 1991, 63, 732–739), or hyphenated techniques such as LC-MS (Bruins, Covey and Henion, Anal. Chem., 1987, 59, 2642–2646 Huang and Henion, J. Am. Soc. Mass Spectrom., 1990, 1, 158–65; Huang and Henion, Anal. Chem., 1991, 63, 732–739) and CE-MS (Cai and Henion, J. Chromatogr., 1995, 703, 667–692) experiments. FTICR-MS has also been applied to the study of ion-molecule reaction pathways and kinetics.

So-called "Hyphenated" techniques can be used for structure elucidation because they provide the dual features of separation and mass detection. Such techniques have been used for the separation and identification of certain components of mixtures of compounds such as those isolated from natural products, synthetic reactions, or combinatorial chemistry. Hyphenated techniques typically use a separation method as the first step; liquid chromatography methods such as HPLC, microbore LC, microcapillary LC, or capillary electrophoresis are typical separation methods used to separate the components of such mixtures. Many of these separation methods are rapid and offer high resolution of components while also operating at low flow rates that are compatible with MS detection. In those cases where flow rates are higher, the use of 'megaflow' ESI sources and sample splitting techniques have facilitated their implementation with on-line mass spectrometry. The second stage of these hyphenated analytical techniques involves the injection of separated components directly into a mass spectrometer, so that the spectrometer serves as a detector that provides information about the mass and composition of the materials separated in the first stage. While these techniques are valuable from the standpoint of gaining an understanding of the masses of the various components of multicomponent samples, they are incapable of providing structural detail. Some structural detail, however, may be ascertained through the use of tandem mass spectrometry, e.g., hydrogen/deuterium exchange or collision induced disassociation.

Typically, tandem mass spectrometry ($MS^n$) involves the coupled use of two or more stages of mass analysis where both the separation and detection steps are based on mass spectrometry. The first stage is used to select an ion or component of a sample from which further structural information is to be obtained. This selected ion is then fragmented by (CID) or photodissociation. The second stage of mass analysis is then used to detect and measure the mass of the resulting fragments or product ions. The advent of FTICR-MS has made a significant impact on the utility of tandem, $MS^n$ procedures because of the ability of FTICR to select and trap specific ions of interest and its high resolution and sensitivity when detecting fragment ions. Such ion selection followed by fragmentation routines can be performed multiple times so as to essentially completely dissect the molecular structure of a sample. A two-stage tandem MS experiment would be called a MS-MS experiment while an n-stage tandem MS experiment would be referred to as a $MS^n$ experiment. Depending on the complexity of the sample and the level of structural detail desired, $MS^n$ experiments at values of n greater than 2 may be performed.

Ion trap-based mass spectrometers are particularly well suited for such tandem experiments because the dissociation and measurement steps are temporarily rather than spatially separated. For example, a common platform on which tandem mass spectrometry is performed is a triple quadrupole mass spectrometer. The first and third quadrupoles serve as mass filters while the second quadrupole serves as a collision cell for CAD. In a trap based mass spectrometer, parent ion selection and dissociation take place in the same part of the vacuum chamber and are effected by control of the radio frequency wavelengths applied to the trapping elements and the collision gas pressure. Hence, while a triple quadrupole mass analyzer is limited to two stages of mass spectrometry (i.e. MS/MS), ion trap-based mass spectrometers can perform $MS^n$ analysis in which the parent ion is isolated, dissociated, mass analyzed and a fragment ion of interest is isolated, further dissociated, and mass analyzed and so on. A number of $MS^n$ procedures and higher have appeared in the literature in recent years and can be used here. (Cheng et al., Techniques in Protein Chemistry, VII, pp. 13–21).

ESI and MALDI techniques have found application for the rapid and straightforward determination of the molecular weight of certain biomolecules (Feng and Konishi, Anal. Chem., 1992, 64, 2090–2095; Nelson, Dogruel and Williams, Rapid Commun. Mass Spectrom., 1994, 8, 627–631). These techniques have been used to confirm the identity and integrity of certain biomolecules such as peptides, proteins, oligonucleotides, nucleic acids, glycoproteins, oligosaccharides and carbohydrates. Further, these MS techniques have found biochemical applications in the detection and identification of post-translational modifications on proteins. Verification of DNA and RNA sequences that are less than 100 bases in length has also been accomplished using ESI with FTMS to measure the molecular weight of the nucleic acids (Little et al, Proc. Natl. Acad. Sci. USA, 1995, 92, 2318–2322).

ESI tandem MS has been used for the study of high molecular weight proteins, for peptide and protein sequencing, identification of post-translational modifications such as phosphorylation, sulfation or glycosylation, and for the study of enzyme mechanisms (Rossomando et al., Proc. Natl. Acad. Sci. USA, 1992, 89, 5779–578; Knight et al., Biochemistry, 1993, 32, 2031–2035). Covalent enzyme-intermediate or enzyme-inhibitor complexes have been detected using ESI and analyzed by ESI-MS to ascertain the site(s) of modification on the enzyme. The literature has shown examples of protein sequencing where the multiply charged ions of the intact protein are subjected to collisionally activated dissociation to afford sequence informative fragment ions (Light-Wahl et al., Biol. Mass Spectrom., 1993, 22, 112–120). ESI tandem MS has also been applied to the study of oligonucleotides and nucleic acids (Ni et al., Anal. Chem., 1996, 68, 1989–1999; Little, Thannhauser and McLafferty, Proc. Natl. Acad. Sci., 1995, 92, 2318–2322).

While tandem ESI mass spectra of oligonucleotides are often complex, several groups have successfully applied ESI tandem MS to the sequencing of large oligonucleotides (McLuckey, Van Berkel and Glish, J. Am. Soc. Mass Spectrom., 1992, 3, 60–70; McLuckey and Habibigoudarzi, J. Am. Chem. Soc., 1993, 115, 12085–12095; Little et al., J. Am. Chem. Soc., 1994, 116, 4893–4897). General rules for the principal dissociation pathways of oligonucleotides, as formulated by McLuckey (McLuckey, Van Berkel and Glish, J. Am. Soc. Mass Spectrom., 1992, 3, 60–70; Mcluckey and Habibigoudarzi, J. Am. Chem. Soc., 1993, 115, 12085–12095), have assisted interpretation of mass spectra of oligonucleotides, and include observations of fragmentation such as, for example, the stepwise loss of base followed by cleavage of the 3'—C—O bond of the relevant sugar. Besides the use of ESI with tandem MS for oligonucleotide sequencing, two other mass spectrometric methods are also available: mass analysis of products of enzymatic cleavage of oligonucleotides (Pieles et al., Nucleic Acids Res., 1993, 21, 3191–3196; Shaler et al., Rapid Commun. Mass Spectrom., 1995, 9, 942–947; Glover et al., Rapid Commun. Mass Spectrom., 1995, 9, 897–901), and the mass analysis of fragment ions arising from the initial ionization/desorption event, without the use of mass selection techniques (Little et al., Anal. Chem., 1994, 66, 2809–2815; Nordhoff et al., J. Mass Spectrom., 1995, 30, 99–112; Little et al., J. Am. Chem. Soc., 1994, 116, 4893–4897; Little and McLafferty, J. Am. Chem. Soc., 1995, 117, 6783–6784). While determining the sequence of deoxyribonucleic acids (DNA) is possible using ESI-MS and CID techniques (McLuckey, Van Berkel and Glish, J. Am. Soc. Mass Spectrom., 1992, 3, 60–70; McLuckey and Habibigoudarzi, J. Am. Chem. Soc., 1993, 115, 12085–12095), the determination of RNA sequence is much more difficult. Thus while small RNA, such as 6-mers, have been sequenced (McCloskey et al., J. Am. Chem. Soc., 1993, 115, 12085–1095), larger RNA have been difficult to sequence using mass spectrometry.

Electrospray mass spectrometry has been used to study biochemical interactions of biopolymers such as enzymes, proteins and nucleic acids with their ligands, receptors, substrates or inhibitors. While interactions that lead to covalent modification of the biopolymer have been studied for some time, those interactions that are of a non-covalent nature have been particularly difficult to study heretofore by methods other than kinetic techniques. It is now possible to yield information on the stoichiometry and nature of such non-covalent interactions from mass spectrometry. MS can provide information about the interactions between biopolymers and other molecules in the gas phase; however, experiments have demonstrated that the data so generated can be reflective of the solution phase phenomena from which the mass spectra were generated.

ESI is a gentle ionization method that results in no significant molecular fragmentation and preserves even weakly bound complexes between biopolymers and other molecules so that they are detected intact with mass spectrometry. A variety of non-covalent complexes of biomolecules have been studied using ESI-MS and reported in the literature (Loo, Bioconjugate Chemistry, 1995, 6, 644–665; Smith et al., J. Biol. Mass Spectrom. 1993, 22, 493–501; Li et al., J. Am. Chem. Soc., 1993, 115, 8409–8413). These include the peptide-protein complexes (Busman et al., Rapid Commun. Mass Spectrom., 1994, 8, 211–216; Loo, Holsworth and Root-Bernstein, Biol. Mass Spectrom., 1994, 23, 6–12; Anderegg and Wagner, J. Am. Chem. Soc., 1995, 117, 1374–1377; Baczynskyj, Bronson and Kubiak., Rapid Commun. Mass Spectrom., 1994, 8, 280–286), interactions of polypeptides and metals (Loo, Hu and Smith, J. Am. Soc. Mass Spectrom., 1994, 5, 959–965; Hu and Loo, J. Mass Spectrom., 1995, 30, 1076–1079; Witkowska et al., J. Am. Chem. Soc., 1995, 117, 3319–3324; Lane et al., J. Cell Biol., 1994, 125, 929–943), protein-small molecule complexes (Ganem and Henion, ChemTracts-Org. Chem., 1993, 6, 1–22; Henion et al., Ther. Drug Monit., 1993, 15, 563–569; Baca and Kent, J. Am. Chem. Soc., 1992, 114, 3992–3993), the study of the quaternary structure of multimeric proteins (Baca and Kent, J. Am. Chem. Soc., 1992, 114, 3992–3993; Light-Wahl, Schwartz and Smith, J. Am. Chem. Soc., 1994, 116, 5271–5278; Loo, J. Mass Spectrom., 1995, 30, 180–183), and the study of nucleic acid complexes (Light-Wahl et al., J. Am. Chem. Soc., 1993, 115, 803–804; Gale et al., J. Am. Chem. Soc., 1994, 116, 6027–6028; Goodlett et al., Biol. Mass Spectrom., 1993, 22, 181–183; Ganem, Li and Henion, Tet. Lett., 1993, 34, 1445–1448; Doctycz et al., Anal. Chem., 1994, 66, 3416–3422; Bayer et al., Anal. Chem., 1994, 66, 3858–3863; Greig et al., J. Am. Chem. Soc., 1995, 117, 10765–766).

While data generated and conclusions reached from ESI-MS studies for weak non-covalent interactions generally reflect, to some extent, the nature of the interaction found in the solution-phase, it has been pointed out in the literature that control experiments are necessary to rule out the possibility of ubiquitous non-specific interactions (Smith and Light-Wahl, Biol. Mass Spectrom., 1993, 22, 493–501). Some have applied the use of ESI-MS and MALDI-MS to the study of multimeric proteins for the gentleness of the electrospray/desorption process allows weakly bound complexes, held together by hydrogen bonding, hydrophobic and/or ionic interactions, to remain intact upon transfer to the gas phase. The literature shows that not only do ESI-MS data from gas-phase studies reflect the non-covalent interactions found in solution, but that the strength of such interactions may also be determined. The binding constants for the interaction of various peptide inhibitors to src SH2 domain protein, as determined by ESI-MS, were found to be consistent with their measured solution phase binding constants (Loo, Hu and Thanabal, Proc. $43^{rd}$ ASMS Conf. on Mass Spectrom. and Allied Topics, 1995). ESI-MS has also been used to generate Scatchard plots for measuring the binding constants of vancomycin antibiotics with tripeptide ligands (Lim et al., J. Mass Spectrom., 1995, 30, 708–714).

Similar experiments have been performed to study non-covalent interactions of nucleic acids. Both ESI-MS and MALDI-MS have been applied to study the non-covalent interactions of nucleic acids and proteins. While MALDI does not typically allow for survival of an intact non-covalent complex, the use of crosslinking methods to generate covalent bonds between the components of the complex allows for its use in such studies. Stoichiometry of interaction and the sites of interaction have been ascertained for nucleic acid-protein interactions (Jensen et al., Rapid Commun. Mass Spectrom., 1993, 7, 496–501; Jensen et al., $42^{nd}$ ASMS Conf. on Mass Spectrom. and Allied Topics, 1994, 923). The sites of interaction are typically determined by proteolysis of either the non-covalent or covalently crosslinked complex (Jensen et al., Rapid Commun. Mass Spectrom., 1993, 7, 496–501; Jensen et al., $42^{nd}$ ASMS Conf. on Mass Spectrom. and Allied Topics, 1994, 923; Cohen et al., Protein Sci., 1995, 4, 1088–1099). Comparison of the mass spectra with those generated from proteolysis of the protein alone provides information about cleavage site accessibility or protection in the nucleic acid-protein complex and, therefore, information about the portions of these biopolymers that interact in the complex.

Electrospray mass spectrometry has also been effectively used for the determination of binding constants of noncovalent macromolecular complexes such as those between proteins and ligands, enzymes and inhibitors, and proteins and nucleic acids. Greig et al. (J. Am. Chem. Soc., 1995, 117, 10765–10766) have reported the use of ESI-MS to determine the dissociation constants (KD) for oligonucleotide-bovine serum albumin (BSA) complexes. The KD values determined by ESI-MS were reported to match solution $K_D$ values obtained using capillary electrophoresis.

Cheng et al. (J. Am. Chem. Soc., 1995, 117, 8859–8860) have reported the use of ESI-FTICR mass spectrometry as a method to determine the structure and relative binding constants for a mixture of competitive inhibitors of the enzyme carbonic anhydrase. Using a single ESI-FTICR-MS experiment these researchers were able to ascertain the relative binding constants for the noncovalent interactions between inhibitors and the enzyme by measuring the relative abundances of the ions of these noncovalent complexes. Further, the $K_D$s so determined for these compounds paralleled their known binding constants in solution. The method was also capable of identifying the structures of tight binding ligands from small mixtures of inhibitors based on the high resolution capabilities and multistep dissociation mass spectrometry afforded by the FTICR technique. In a related study, Gao et al. (J. Med. Chem., 1996, 39, 1949–55) have reported the use of ESI-FTICR-MS to screen libraries of soluble peptides in a search for tight binding inhibitors of carbonic anhydrase II. Simultaneous identification of the structure of a tight binding peptide inhibitor and determination of its binding constant was performed. The binding affinities determined from mass spectral ion abundance were found to correlate well with those determined in solution experiments. Further, the applicability of this technique to drug discovery efforts is limited by the lack of information generated with regards to sites and mode of such noncovalent interactions between a protein and ligands.

Also, these methods discuss, and appear to be limited to, the study of ligand interactions with proteins. The suitability of this method of mass spectrometric analysis of binding and dissociation constants for the study of noncovalent interactions of oligonucleotides, nucleic acids, such as RNA and DNA, and other biopolymers has not been described in the literature.

The drug discovery process has recently been revolutionized by the introduction of high throughput synthesis and combinatorial chemistry which afford collections and mixtures of large numbers of synthetic compounds for the purpose of screening for biological activity. Such large mixtures and pools of compounds pose significant challenges for the bioassay and analytical scientist. The analytical challenge is two-fold: separation of the active component of a mixture, and the identification of its structure. A variety of separation methods are available, including LC, HPLC, and CE. However, from the standpoint of separating biologically active components from a mixture of one or more targets with a combinatorial library necessitates the use and development of methods that select for and separate the complex (usually noncovalent) between the ligands and the target. Affinity column methods have been used to selectively isolate and subsequently analyze binding components of mixtures of compounds. For example, Kassel et al. (Kassel et al., Techniques in Protein Chemistry VI, J. Crabb, Ed., Academic Press, San Diego, 1995, 39–46) have used an immobilized src SH2 domain protein column to separate and then analyze by HPLC-ESI-MS the structure of high affinity binding phosphopeptides.

A similar technique, ACE-ESI-MS, uses affinity capillary electrophoresis to accomplish the separation of noncovalent complexes formed upon mixing a biomolecular target with a combinatorial library or mixture of compounds. The receptor is typically incorporated into the capillary so that those ligands present in the combinatorial mixture interact with the target and are retained or slowed down within the capillary. Once separated, these noncovalent complexes are analyzed on-line by ESI-MS to ascertain the structures of the complexes and bound components. This method incorporates into one, the two steps that were previously performed separately: the compound/noncovalent complex selection, as has previously been demonstrated for vancomycin (Chu et al., Acc. Chem. Res., 1995, 28, 461–468; Chu et al., J. Org. Chem., 1993, 58, 648–52) and the step of compound identification (Cai and Henion, J. Chromatogr., 1995, 703, 667–692). For example, ACE-ESI-MS has been applied to mixtures of vancomycin with peptide libraries (Chu et al., J. Am. Chem. Soc., 1996, 118, 7827–35) to allow rapid screening of noncovalent complexes formed, and the identification of peptides that bind to vancomycin.

Another method for the separation and identification of active components from combinatorial libraries is the use of size-exclusion chromatography (SEC) followed by LC/MS or CE/MS analysis. Size exclusion is a simple yet powerful method to separate a biopolymer target and its complexes with small molecules members of a combinatorial library. Once isolated by SEC, these complexes are dissociated, under denaturing solution conditions, and finally the binding ligands are analyzed by mass spectrometry. This method has been applied to the identification of high affinity ligands for human serum albumin (HSA) from combinatorial library of small molecules (Dunayevskiy et al., Rapid Commun. Mass Spectrom., 1997, 11, 1178–84).

Bio-affinity characterization mass spectrometry (BACMS) is yet another method for the characterization of noncovalent interactions of mixtures of ligands and biomolecular targets (Bruce et al., Rapid Commun. Mass Spectrom., 1995, 9, 644–50). BACMS involves the electrospray ionization of a solution containing both the affinity target and a mixture of ligands (or a combinatorial library), followed by trapping of all the ionic species in the FTICR ion-trap. The complexes of interest are then identified in the mass spectrum and isolated by selected-ion accumulation. This is followed by low energy dissociation or 'heating' to separate the high binding affinity ligands present in the complex. Finally, collisionally activated dissociation (CAD) is used to provide structural information about the high binding affinity ligand. The greatest advantage of BACMS is that the time-consuming techniques usually needed for the study of libraries, such as affinity chromatography, using solid supports for separation and purification of the complexes, followed by analysis to characterize the selected ligands, are all combined into one FTICR-MS experiment. To date, BACMS has only been applied to the study of protein targets.

None of the foregoing methods, however, have demonstrated applicability to a variety of biomolecular targets. Further, such methods do not provide rapid determination of the site of interaction between a combinatorially derived ligand and biopolymer.

Tandem mass spectrometry, as performed using electrospray ionization (ESI) on FTICR, triple quadrupole, or ion-trap mass spectrometers, has been found to be a powerful tool for determining the structure of biomolecules. It is known in the art that both small and large (>3000 kbase) RNA and DNA may be transferred from solution into the gas phase as intact ions using electrospray techniques. Further it is known, to those skilled in the art that these ions retain some degree of their solution structures as ions in the gas phase; this is especially useful when studying noncovalent complexes of nucleic acids and proteins, and nucleic acids and small molecules by mass spectrometric techniques.

SUMMARY OF CERTAIN PREFERRED EMBODIMENTS

Studies have demonstrated that oligonucleotides and nucleic acids obey certain fragmentation patterns during collisionally induced dissociation (CID), and that these fragments and patterns can be used to determine the sequence of the nucleic McLuckey, Van Berkel and Glish, J. Am. Soc. Mass Spectrom., 1992, 3, 60–70; Mcluckey and Habibigoudarzi, J. Am. Chem. Soc., 1993, 115, 12085–12095). Electrospray ionization produces several multiply charged ions of the parent nucleic acid, without any significant fragmentation of the nucleic acid. Typically, a single charge state of the nucleic acid is isolated using a triple quadrupole ion trap, or ion cyclotron resonance (ICR) device. This ion is then excited and allowed to collide with a neutral gas such as helium, argon or nitrogen so as to afford cleavage of certain bonds in the nucleic acid ion, or excited and fragmented with a laser pulse. Typically, two series of fragment ions are found to be formed: the a-Base series, and the w-series.

The series of a-Base fragments originates from initial cleavage of the glycosidic bond by simultaneous abstraction of a C-2' proton, followed by the elimination of the 3'-phosphate group and the C-4' proton. This fragmentation scheme results in a residual furan attached to the 3'-phosphate and affords a series of a-Base fragments whose masses increase sequentially from the 5'-terminus of the nucleic acid. Measurement of the masses of these collisionally induced fragments therefore affords the determination of the sequence of the nucleic acid in the 5' to 3' direction. The w series of fragments is generated via cleavage of the nucleic acid in a manner that leaves a 5' phosphate residue on each fragment. Thus monitoring the masses of w-series fragments allows determination of the sequence of the nucleic acid in the 3' to 5' direction. Using the sequence information generated from both series of fragments the sequence of deoxyribonucleic acids (DNA) may be ascertained. Obtaining similar mass spectrometric information for ribonucleic acids (RNA), is a much more difficult task. Collisionally induced dissociation (CID) of RNA is much less energetically favored than is the case for DNA because of the greater strength of the glycosidic bond in RNA. Hence, while small RNA such as 6-mers have been sequenced using CID MS, the sequencing of larger RNA has not been generally successful using tandem MS.

Determination of the structure of biomolecules, such as proteins and nucleic acids, may be attempted using solution biochemical cleavage followed by mass spectrometry. However, these methods are cumbersome and not always successful in that several biochemical cleavage and separation steps need to be performed prior to MS analysis of the cleaved products. Also, the level of information provided with regards to secondary and tertiary structure of biomolecules is limited. Methods available in the scientific literature are therefore greatly limited in terms of the sequence and structural information they provide for biomolecules and biomolecular targets.

One aspect of the present invention provides methods for determining the structure of biomolecular targets such as nucleic acids using mass spectrometry. The structure of nucleic acids, especially RNA, which is often difficult to ascertain, is readily determined using the methods of this invention. The structure of a nucleic acid is determined from the fragmentation pattern observed in $MS^n$ experiments. Directed fragmentation of RNA is facilitated by the selective incorporation of deoxynucleotides or other nucleosidic residues at specific residue locations in the nucleic acid sequence. During CID of such RNA/DNA chimeric nucleic acids, cleavage is facilitated at the sites where deoxynucleotides or the other non-native residues were incorporated. Cleavage is also influenced by the local secondary and tertiary structure of the biomolecule. Therefore, the cleavage patterns observed from a RNA/DNA hybrid reveals the local structure of the nucleic acid, including mismatched base pairs, bulged regions and other features.

Since exposed deoxynucleotide residues are known to be susceptible to CID cleavage in MS experiments, the systematic incorporation of such residues into RNA allows the systematic exploration of the local structure of RNA. Using this embodiment of the invention, it is possible to determine the secondary and tertiary structure of nucleic acids, including features such as mismatched base pairs, loops, bulges, and kink and stem structures.

Determination of the structure of an RNA may be accomplished, using exemplary methods of the invention, as follows. An RNA whose structure is to be determined is synthesized using an automated nucleic acid synthesizer. During RNA synthesis, deoxynucleotides are selectively incorporated into the sequence at specific sites where the structure is to be probed. This RNA/DNA chimeric nucleic acid, which is sensitized to collisional activation, is now used for sequence and structure determination using tandem MS experiments. ESI-MS, followed by trapping of selected ions and subsequent CID of each ion, affords information as to which positions of the nucleic acid hybrid are disordered (or not participating in a higher order structure) and, therefore, available for cleavage. A systematic pattern of deoxynucleotide incorporation into the sequence of the test RNA allows a systematic, mass spectrometric assessment of structure in a certain area of the nucleic acid, or for the entire nucleic acid. Other modified nucleic acid residues may be used instead of DNA. This, chemically modified nucleic acid subunits such as $Z^1$-modified, e.g. $2^1$-OAlky, base-modified, backbone modified or other residues may serve. Such residues will permit assessment of DNA as well as RNA.

The present invention also provides methods for the determination of the site and nature of interactions between a biomolecular target and a binding ligand. This is information of critical value to the process of drug discovery. Current methods of biomolecular screening do not provide a straightforward means of also determining the nature of the interaction between a binding ligand and the biomolecular target. Information such as the stoichiometry and binding affinity of the interaction often needs to be ascertained from additional biochemical assays, thus slowing down and increasing the cost of drug discovery. It is often the case that binding of a drug or ligand to a biomolecular target, such as a nucleic acid, may lead to a change in conformation of the biomolecule to a different structure. This, too, may contribute to protection of the biomolecule from cleavage.

The present invention provides convenient methods for determining the site or sites on a biomolecular target where a binding ligand interacts. This is accomplished based on the knowledge that collisionally activated dissociation (CID or CAD) of a noncovalent biomolecule-ligand complex may be performed such that cleavage of the complex occurs only at exposed sites of the biomolecules. Thus cleavage sites present on the biomolecule that are involved in binding with the ligand are protected because of the increased structural order from the binding event during CID. ESI-$MS^n$ spectra generated using this method, in the presence and absence of a binding ligand (or drug), will reveal differential fragmentation patterns due to ligand induced protection of cleavage sites. Comparison of the mass spectra generated in the presence and absence of a binding ligand will, therefore, reveal the positions in the biomolecular sequence where the interactions between ligand and biomolecule are occurring.

These methods for determining the sites of interaction between a binding ligand and a biomolecular target are broadly applicable. The biomolecular targets that may be studied using this method include, but are not limited to, peptides, proteins, antibodies, oligonucleotides, RNA, DNA, other nucleic acids, glycopeptides, and oligosaccharides. It is preferred that the biomolecular target be a nucleic acid. It is further preferred that the biomolecular target be a chimeric RNA/DNA nucleic acid, synthesized to selectively incorporate deoxynucleotides, (or other residues) in the sequence at specific locations. The binding ligand may be one of the groups of molecules including, but not limited to, organic or inorganic, small to large molecular weight individual compounds, mixtures and combinatorial libraries of ligands, inhibitors, agonists, antagonists, substrates, and biopolymers, such as peptides or oligonucleotides.

Determination of the sites on an RNA target where interaction occurs with a binding ligand may be accomplished as follows. An RNA target that is to be studied as a biomolecular target is prepared using an automated synthesizer, and selectively incorporating deoxynucleotides into the sequence at specific sites. An aliquot of this RNA/DNA chimeric is used directly for ESI-MS, followed by CID analysis of selectively accumulated ions, to establish the native structure and cleavage patterns of this biomolecular target. A second aliquot of the RNA/DNA chimeric is mixed with a solution of a drug or ligand that is known to bind to the biomolecular target. The target and ligand are anticipated to interact in solution to form a noncovalent complex. Subjecting this solution of the noncovalent biomolecule-ligand complex to the method of this invention leads to ionization of the complex with a retention of the noncovalent interactions and binding stoichiometries. CID of the complex then leads to cleavage of the biomolecule sequence at fragmentation sites that are exposed. Sites where fragmentation would otherwise occur, but which are involved in binding the ligand to the biomolecule, are protected, such that cleavage at or near these sites is prevented during the CID stage. The differences in the fragmentation patterns of the biomolecule when subjected to the methods of this invention in the presence and absence of binding ligand indicate the site(s) on the biomolecule that is protected and, therefore, are involved in binding the ligand.

Likewise, a systematic pattern of deoxynucleotide incorporation into the sequence of the test RNA will allow for a systematic mass spectrometric assessment of binding sites and interactions in a certain area of the nucleic acid, or for the entire nucleic acid, using the method of this invention. This invention, therefore, also provides a new method of 'footprinting' biomolecular targets especially nucleic acids. This footprinting by mass spectrometry is a straightforward method for mapping the structure of biomolecular targets and the sites of interactions of ligands with these targets.

The nature of interactions between the binding ligand and a biomolecular target are also readily studied using the method of this invention. Thus, the stoichiometry and relative dissociation constant of the biomolecule-ligand noncovalent complex is readily ascertained using the method of this invention. The ratio of the number of ligand molecules and the number of biomolecular receptors involved in the formation of a noncovalent biomolecule-ligand complex is of significant importance to the biochemist and medicinal chemist. Likewise, the strength of a noncovalent complex, or the binding affinity of the ligand for the biomolecular target, is of significance because it provides an indication of the degree of complementarity between the ligand and the biomolecule. Also, the determination of this binding affinity is important for the rank ordering of different ligands so as to provide structure-activity relationships for a series of ligands, and to facilitate the design of stronger binding ligands for a particular biomolecular target.

The methods of the present invention are also capable of determining both the binding stoichiometry and affinity of a ligand for the biomolecular target being screened in a screening study. Electrospray ionization is known to retain to a significant degree, the solution phase structures of biomolecules and their noncovalent complexes in the gaseous ions it generates. Thus, determination of the stoichiometry of noncovalent complexes simply needs data on the masses of the ligand, biomolecular target and the noncovalent biomolecule-ligand complex. The data needed to accomplish this determination is actually available from the mass spectrometry experiment that may be performed to determine the structure and site of binding of a ligand to the biomolecular target. Based on the knowledge of the structure and sequence of the target biomolecule, MS analysis of the biomolecule-ligand complex reveals the number of ligand and target molecules present in the noncovalent complex. If the noncovalent complex ion observed from the mass spectrum is of an m/z equal to that expected from the addition of the m/z values of one molecule each of the target biomolecule and ligand, then the noncovalent complex must be formed from a 1:1 interaction between the biomolecule and ligand. Simple mathematical operations on the molecular weight and charges of the target and ligand can likewise determine higher levels of interactions between ligand and biomolecule. The high resolution of a FTICR mass spectrometer allows direct identification of the bound ligand based on exact measurement of the molecular mass of the complex relative to unbound nucleic acid.

The use of mass spectrometry, in accordance with this invention can provide information on not only the mass to charge ratio of ions generated from a sample, but also the relative abundance of such ions. Under standardized experimental conditions, it is therefore possible to compare the abundance of a noncovalent biomolecule-ligand complex ion with the ion abundance of the noncovalent complex formed between a biomolecule and a standard molecule, such as a known substrate or inhibitor. Through this comparison, binding affinity of the ligand for the biomolecule, relative to the known binding of a standard molecule, may be ascertained.

Determination of the nature of the interaction of a ligand with a biomolecular target may be carried out as exemplified for the binding of a small molecule ligand with a nucleic acid target. A chimeric RNA/DNA biomolecular target whose binding to a test ligand is to be studied is first prepared via automated synthesis protocols. An aliquot of a known concentration of chimeric nucleic acid is treated with a known concentration and quantity of a standard compound that is known to bind that nucleic acid, such as the aminoglycoside paromomycin which is known to bind to the 16S A-site of RNA. ESI-MS, followed by CID of the paromomycin-nucleic acid complex, affords a control spectrum for the interactions and complex. A second aliquot of the chimeric nucleic acid is next treated with a test ligand using quantities and concentrations similar to those used for the control experiment. Application of the method of the invention to this nucleic acid-ligand noncovalent complex affords a test spectrum that reveals the nature of the biomolecule-ligand interaction. Analysis of the noncovalent nucleic acid-ligand complex based on the known molecular weights of the two components of the complex allows the determination of the number of nucleic acid molecules and ligands present in the complex. Further, comparison of the abundance of the nucleic acid-ligand complex ion with the abundance of the ion generated from the e.g. paromomycin-nucleic acid complex (or complex with any other known interacting species) provides a convenient and direct estimate of the binding affinity of the test ligand compared to the standard, paromomycin. Since the standard is well characterized, its solution binding affinity should be known from other experiments or literature sources. For example, paromomycin binds to a test 27-mer RNA with a ~1 $\mu$M affinity. Knowing the binding affinity of the test ligand relative to paromomycin from the MS experiment, it is now possible to determine the micromolar binding affinity of the test ligand for the nucleic acid target being studied. Relative binding affinity may also be measured by testing a standard compound and test ligand simultaneously as in a mixture with the target biomolecule, in a single test assay.

Another object of the present invention is to provide general methods for the screening of compounds for drug discovery. The invention provides methods for the screening of a wide variety of biomolecular targets that include, but are not limited to, peptides, proteins, receptors, antibodies, oligonucleotides, RNA, DNA, RNA/DNA hybrids, nucleic acids, oligosaccharides, carbohydrates, and glycopeptides. The molecules that may be screened by using the methods of this invention include, but are not limited to, organic or inorganic, small to large molecular weight individual compounds, mixtures and combinatorial libraries of ligands, inhibitors, agonists, antagonists, substrates, and biopolymers, such as peptides or oligonucleotides.

The primary challenge when screening large collections and mixtures of compounds is not in finding biologically relevant activities, for this has been demonstrated in many different cases, but in identifying the active components from such screens, and often from mixtures and pools of compounds that are found to be active. One solution that has been practiced by the art-skilled in high throughput drug discovery is the iterative deconvolution of mixtures. Deconvolution essentially entails the resynthesis of that combinatorial pool or mixture that was found to be active in screening against a target of interest. Resynthesis may result in the generation of a set of smaller pools or mixtures, or a set of individual compounds. Rescreening and iterative deconvolution are performed until the individual compounds that are responsible for the activity observed in the screens of the parent mixtures are isolated.

However, analytical techniques are limited in their ability to adequately handle the types of mixtures generated in combinatorial efforts. The similarity of members of combinatorial mixtures or pools, and the complexity of such mixtures, prohibit effective analytical assessment until the mixtures have been deconvoluted into individual compounds, or at the very least into pools of only a handful of components. While this process of deconvolution, involving resynthesis, rescreening and analysis, is very cumbersome and time-consuming, it is also very costly. A general method that alleviates these problems by rapidly revealing active mixtures and identifying the active components of such mixtures is clearly needed to save time and money in the drug discovery process.

The present invention solves the need for a method to rapidly assess the activity of combinatorial mixtures against a biomolecular target and also identify the structure of the active components of such mixtures. This is exemplified by the screening of combinatorial mixtures for binding to a nucleic acid target as follows. A chimeric RNA/DNA target of known sequence is selected as the screening target based on biological relevance. This chimeric nucleic acid target is prepared via automated synthesis. An aliquot of the nucleic acid is used at a concentration of 10 µM and treated with e. q. paromomycin acetate at a concentration of 150 nM. A sample of the mixture is analyzed by the method of the invention to demonstrate binding of the paromomycin by observation of the paromomycin-nucleic acid complex ion. Next, an aliquot of this mixture is treated with a DMSO solution of a combinatorial mixture of compounds such that the final concentration of each component of the mixture is ~150 nM. This sample is then subjected to ESI-MS, and the mass spectrum monitored for the appearance of new signals that correspond to new nucleic acid-ligand noncovalent complexes formed with components of the combinatorial library.

The relative dissociation constants of these new complexes are determined by comparing the abundance of these new ions with the abundance of the paromomycin-nucleic acid complex ion whose binding affinity for the target is known a priori. Algorithmic deconvolution of the new complex ions observed, while taking into account the masses of the target and the components of the combinatorial library, provides the molecular weights of the binding ligands present in the observed noncovalent complexes. Alternatively, the identity of the binding ligand may also be determined by first isolating the newly observed complex ion using a triple quadrupole ion-trap or an ion cyclotron resonance device (ICR) followed by conventional identification by mass spectrometry fragment analysis. For example, upon isolation, a noncovalent complex ion is 'heated' or dissociated into the constituent ligand and biomolecule ions. This MS/MS experiment then can be tuned to study fragmentation of the ligand. This information provides direct evidence of the structure of the bound ligand. This method of the present invention, therefore, provides both the identity and relative binding affinity of members of combinatorial or other mixtures of compounds that bind to the nucleic acid target.

Not only does the present invention provide methods for the determination of the molecular weight and relative binding affinity of the binding components of a combinatorial or other mixture of compounds, but it also provides valuable information about the site of binding on the biomolecular target. Such information permits the identification of compounds having particular biological activity and gives rise to useful drugs, veterinary drugs, agricultural chemicals, industrial chemicals, diagnostics and other useful compounds. This can also be accomplished as part of the same mass spectrometric procedure by isolating the newly observed complex ions using a triple quadrupole ion-trap or an ion cyclotron resonance device (ICR). For example, upon isolation, a noncovalent complex ion is collisionally activated to cleave the chimeric nucleic acid target at exposed deoxynucleotide sites. This MS/MS procedure, then, can be tuned to study fragmentation of the biomolecular target.

Comparison of the cleavage and fragment patterns so obtained for the nucleic acid component of the noncovalent complex with patterns obtained for the native chimeric nucleic acid alone reveals the locations on the nucleic acid that are protected by the binding of the ligand. This indicates the binding sites for the ligand on the nucleic acid. Comparison of the cleavage patterns to those observed from the CID of the standard-nucleic acid complex ion provide correlations between the sites of binding of the new ligand and standard. In this fashion, ligands that bind to nucleic acid targets may be identified such that they compete for the same binding site on the nucleic acid where the standard binds, or bind at completely different and new sites on the nucleic acid. Both these types of observations are of value from a drug discovery standpoint.

Drug discovery, using any one of a number of different types of biomolecular targets attends use of the methods of this invention which can rapidly screen large combinatorial libraries and mixtures of compounds for binding activity against a specific target.

It is possible that combinatorial libraries and mixtures of compounds being used for screening may contain components that are similar in mass because their elemental compositions are similar while their structures are different, or at the very least, isomeric or enantiomeric. In such instances, a simple algorithmic calculation of the molecular weight of a bound ligand will be insufficient to provide the identity of the ligand for there may be multiple components of the same molecular mass. The methods of the invention are also capable of addressing and resolving such problems of ligand identification. The use of MS/MS experiments to further fragment the bound ligand, following selective ion accumulation of the ligand ion from the noncovalent complex, is a simple technique that provides structural detail of the bound ligand. This mass and structural information provided by the methods of this invention is expected to resolve the vast majority of mass redundancy problems associated with the screening of large combinatorial libraries and mixtures of compounds.

In a preferred embodiment, the present invention also provides method for simultaneously screening multiple biomolecular targets against combinatorial libraries and mixtures or collections of compounds. This is a significant advantage of the present invention over current state-of-the-art techniques in the screening of compounds for such binding. There is believed to be no prior technique that allows the simultaneous and rapid screening of multiple targets, while providing structural detail on the target and binding ligand at the same time. In addition to providing methods for the rapid and simultaneous screening of multiple biomolecular targets, the present invention also provides methods for determining the structure and nature of binding of both the target and binding ligand.

As discussed above, mass spectrometry methods of the present invention provide a direct means for screening and identifying those components of combinatorial mixtures that bind to a target biomolecule in solution. In order to enhance efficiency, it is preferable to multiplex the screening process by simultaneously screening multiple targets for binding activity against a combinatorial library or mixture of compounds. This strategy is normally limited by the distribution of charge states and the undesirable mass/charge overlap that will be generated from all possible noncovalent biomolecule-ligand complexes that could be formed during such a screening assay. This problem of overlapping peaks in the mass spectra is further exacerbated if the biomolecular targets being screened are of similar sequence, composition, or molecular weight. In such instances it would not be possible to ascertain in a rapid and simple operation the composition of biomolecule-ligand complexes because of the extensive mass redundancy present in the pool of biomolecules being studied and possible in the combinatorial library being screened.

The method of the present invention alleviates the problem of biomolecular target mass redundancy through the use of special mass modifying molecular weight tags. These mass modifying tags are typically uncharged or positively charged groups such as, but not limited to, alkyl and tetraalkylammonium groups, and polymers such as, but not limited to, polyethylene glycols (PEG), polypropylene, polystyrene, cellulose, sephadex, dextrans, cyclodextrins, peptides, and polyacrylamides. These mass modifying tags may be selected based on their molecular weight contribution and their ionic nature. These mass modifying tags may be attached to the biopolymeric targets at one or more sites including, but not limited to, the 2'—O—, 3'-terminus, 5'-terminus or along the sugar-phosphate backbone of nucleic acid targets. Addition of mass modifying tags to the 5'terminus of synthetic oligonucleotides can be realized either using conventional phosphoramidite chemistry, other conventional chemistry or by biochemical or enzymatic means. Such mass modification of a nucleic acid may be carried out using conventional, manual or automated techniques. Alternatively, addition of mass modifying tags may be performed at the 3'-terminus by the use of appropriately modified polymer or CPG supports for solid-phase synthesis of nucleic acids. Mass modification at the 3'terminus may also be done by biochemical or enzymatic means. It is also possible to attach mass modifying tags to the internucleotide linkages of a nucleic acid. This may be performed via the use of appropriately modified phosphoramidites, or other nucleoside building blocks during nucleic acid synthesis or via post-synthetic modification of the internucleotide linkage. Further, attachment of mass modifying tags to nucleic acid targets may also be accomplished via the use of bifunctional linkers at any functional site on the nucleic acid. Similarly, when working with other classes of biomolecular targets these mass modifying tags may likewise be incorporated at one or more positions on the biomolecule. As will be apparent, inclusion in either target or ligand of isotopic mass labels may also be useful.

Thus, similar nucleic acid and other biological targets may be differentially tagged for rapid mass spectrometric screening by the methods of this invention. When noncovalent complexes are observed from this multiplexed screening of multiple nucleic acid targets with mixtures of small molecular weight combinatorial libraries, the constituent ligand and biomolecule are readily identified using conventional mass analyzers such as quadrupole, ion trap, ICR, magnetic sector, or TOF and followed by MS/MS. This is because the mass modifying tags make the m/z (mass to charge ratio) of the signal arising from each target biomolecule-ligand complex ion of similar charge, distinct in the mass spectrum, and which results in cleanly separated ion peaks. Mass redundancy and peak overlap are both avoided by the use of mass modifying tags.

The present invention is also highly useful in combination with other techniques for the identification of ligands which interact with molecular interaction sites on RNA and other nucleic acids. Molecular interaction sites attend RNA and are believe to be highly important in the functioning of such RNA. The nucleotide sequences of molecular interaction sites are highly conserved, even among taxonomically diverse species. Moreover, such molecular interaction sites have specific structures which provide opportunities for ligand binding. Ascertaining which ligands bind to such sites as well as determining the relative affinities and specificities for the binding of each ligand provides lead compounds for drug discovery, therapeutics, agricultural chemistry, industrial chemistry and otherwise.

The present mass spectrometric techniques, especially the MASS techniques and those which possess similar analytical robustness and power, are ideally suited for cooperating with drug and other discovery and identification programs such as those which determine ligand binding to molecular interaction sites. The identification of molecular interaction sites in RNA and other nucleic acids and the determination of hierarchies of molecular ligands which likely bind to such molecular interaction sites can be evaluated through the present techniques. Thus, in accordance with preferred embodiments of the present invention, a hierarchy of ligands ranked in accordance with their anticipated or calculated likelihood of binding to a molecular interaction site of an RNA are actually synthesized. Such synthesis is preferably accomplished in an automated or robotized fashion, preferably from instruction sets provided in attendance to the ranked hierarchy of ligands. The compounds may be prepared in a library or mixture since the present mass spectrometric methods can evaluate pluralities of compounds and their complexes with RNA simultaneously.

After the ligands are synthesized, preferably in library form, they are contacted with the RNA having the molecular interaction site of interest. Complexation or binding (conventionally, non-covalent binding) is permmitted to occur. The complexed RNA—ligand library is then analyzed by mass spectrometry. A principal object of the analysis is preferably the determination of which ligands bind to the RNA molecular interaction site and, among those, which ones rank more highly in terms of specificity and affinity. Accordingly, it is possible to identify from a mixture or library of compounds, which ones are the most interactive with a particular molecular interaction site so as to be able to modulate it. Such compounds can either be used themselves, or, more likely, be used as lead compounds for modification into drugs, agricultural chemicals, environmental chemicals, industrial and food chemicals and otherwise.

As described above, it is highly desirable to challenge RNAs having molecular interaction sites with libraries of compounds which have already been predicted or calculated to be likely to interact with the interaction sites. It is preferred that such molecules belong to ranked hierarchies so as to give rise to the greatest likelihood of finding highly potent modulators of the target RNA.

While there are a number of ways to identify compounds likely to interact with molecular interaction sites of RNA and other biological molecules, preferred methodologies are described in U.S. Pat. Nos. 6,221,587 and 6,253,168 and in applications having U.S. Ser. Nos. 09/076,447 (now abandoned), 09/076,214, and 09/076,404. All of the foregoing applications are incorporated by reference herein in their entirety.

One mass spectrometric method which is particularly useful when combined with the techniques of the foregoing commonly owned inventions provides the determination of specificity and affinity of ligands to RNA targets. MASS (multi target affinity/specificity screening) techniques can provide high throughput screening methods to analyze the specificity and affinity of ligands to molecular interaction sites of nucleic acids, especially RNA. MASS employs high performance electrospray ionization Fourier transform ion cyclotron resonance mass spectrometry (ESI-FTICR-MS) to a) determine exact chemical composition of affinity selected ligands originating from a combinatorial library, b) determine relative dissociation constants (Kd) of ligands complexed to the target(s), and c) determine the location of ligand binding. This information can be gathered from each target(s) or library set in a single assay in less than 15 minutes. This scheme benefits from two unique aspects of the ESI-FTICR combination. The "soft" nature of the electrospray ionization process allows specific noncovalent complexes to be ionized and transferred into the gas phase intact where they are amenable to subsequent characterization by mass spectrometry. The high resolving power afforded by the FTICR platform facilitates the characterization of complex mixtures which, when combined with the high mass accuracy inherent to FTICR, provides unambiguous identification of ligands complexed with the molecular interaction site or sites of a target or targets.

Binding site information can be obtained by comparing the gas phase fragmentation patterns of the free and complexed target while relative binding constants are derived from the relative abundance of complexes using a complex with a known Kd as an internal standard. With knowledge of the specificity and affinity of ligands to the molecular interaction site of a target RNA, the desired lead or ultimate compound for modulation of the RNA can be determined. Therapeutic, agricultural chemical, industrial chemical and other products which benefit from modulation of such RNA attend this result.

The simultaneous screening of a combinatorial library of molecules of mass 700–750, against two nucleic acid targets of the same molecular weight but different sequence, is demonstrated by the use of mass modifying tags. If both nucleic acids targets being studied are 27-mer RNAs of mass 8927, then screening a library of molecules of mass 700–750 could afford a bewildering jumble of noncovalent complex ions in the mass spectrum of the mixture of the two nucleic acids and the library. However if one of the two targets is mass modified, for example by the use of a PEG chain of mass 3575 attached at the 5'terminus of the target, then the mass spectrum will be significantly simplified. It is known that a 27-mer will generate multiply-charged ion signals, following electrospray ionization, of mass/charge values 1486.8, 1784.4, and 2230.8 for the $(M-6H)^{6-}$, $(M-5H)^{5-}$, and the $(M-4H)^{4-}$ charge states. Upon binding to small molecules of mass 700–750, the unmodified RNA-ligand complexes are anticipated to occur in the 1603.2–1611.6, 1924.4–1934.4, and 2405.8–2418.3 m/z range. If the second nucleic acid target were not modified in any way, the signals from its complexes would have occurred in the same regions. However, using the mass modified RNA, bearing the PEG chain of mass 3575, results in the observation of the corresponding mass modified RNA-ligand complexes to occur in the 2199–2207.4, 2639–2649 and 3299–3311 m/z range. Thus all signals from the second mass modified nucleic acid would be cleanly resolved from those of the first RNA. These noncovalent complex ions may be selected e.g. by triple, quadrupole, ion trap or ICR techniques, and studied further by MS/MS to afford detailed understanding of the sites of ligand-RNA interaction, and the nature of these interactions, as has been discussed above.

In a further embodiment, the methods of this invention are applicable for the determination of the specificity of binding interactions between a ligand and a biomolecular target. By simultaneously screening multiple biomolecular targets with one or more compounds, using the methods of this invention, it is possible to ascertain whether a ligand binds specifically to only one target biomolecule, or whether the binding observed with the target is reproduced with control biomolecules as well, and is therefore non-specific. This is an important distinction to be made when screening large libraries and collections of compounds for binding to biomolecular targets. It is desirable to quickly distinguish those ligands that are selective or specific for the biomolecular target of interest from those that are non-specific and bind to any and all targets. From the standpoint of drug discovery, it is most often the case that undesirable biological activities arise from the indiscriminate, non-specific binding of molecules to unrelated biomolecules. The present invention provides a valuable and straightforward method for assessing the specificity of interactions between a ligand and a panel of targets.

The use of mass modifying tags for the simultaneous screening of multiple biomolecular targets is applicable to the determination of binding specificity of a ligand as well. Mass modifying tags may be used to differentiate several biomolecular targets that serve as a control panel for screening a combinatorial library of individual compounds against a specific biomolecular target. When simultaneously screening multiple biomolecular targets using the mass spectrometric methods of this invention, it is necessary to ensure good separation of the ions that result from each target and its complex with the binding ligand. This peak overlap is easily eliminated by the facile introduction of different mass modifying tags onto the different biomolecular targets being studied. A mixture of the biomolecular target and the control panel is mixed with the ligand being evaluated. This solution is then ionized by ESI-MS, and the noncovalent complex ions observed may be directly identified as having resulted from the binding of the ligand to a specific target from the several biomolecular targets present in the mixture. In this way, a qualitative indication of specificity or selectivity of binding for the desired target versus the control biomolecules may be obtained. This selectivity may also be quantitated through the use of appropriate standards of known binding affinity and comparison of the ligand-biomolecule complex ion abundance to the abundance of the standard-biomolecule abundance. Further, details on the nature of the specific or non-specific interaction of the ligand with the different biomolecules may also be obtained following ion-selection and subsequent MS/MS experiments, as discussed above.

Likewise, it is also possible to determine the proportional binding of a ligand to two or more biomolecular targets using the methods of this invention. Thus by the use of appropriate mass modifying tags on the different biomolecular targets, the different noncovalent complexes formed via differential binding of the ligand can be readily distinguished in the mass spectrometer. Quantitation of the binding is possible by measuring the abundance of these ions. Comparing the relative abundances of these ions provides a means to determine the proportional binding of the ligand to the different biomolecular targets.

Yet another application of the methods of the present invention is to determine the differential binding of ligands to biomolecular targets of different origin. When studying the binding of small molecule ligands to RNA targets, it is straightforward to distinguish between the noncovalent ligand-RNA complexes generated from binding to the two different RNA targets, even though both may be screened simultaneously as a mixture in the same assay. Further, it is also possible to determine specificity and selectivity of the ligand for one versus the other RNA, and to determine the relative affinities of binding to each RNA target.

The methods of the present invention are applicable to the study of a wide variety of biomolecular targets that include, but are not limited to, peptides, proteins, receptors, antibodies, oligonucleotides, RNA, DNA, RNA/DNA hybrids, nucleic acids, modified oligonucleotides, peptide-nucleic acids (PNAs), oligosaccharides, carbohydrates, and glycopeptides. Further these biomolecular targets may be synthetic or isolated from natural sources. Biomolecular targets of natural origin include, but are not limited to, those obtained from microbial, plant, animal, viral or human materials, such as, but not limited to, cells, cell extracts, fluids, tissues and organs.

The molecules that may be screened by using the methods of this invention include, but are not limited to, organic or inorganic, small to large molecular weight individual compounds, and combinatorial mixture or libraries of ligands, inhibitors, agonists, antagonists, substrates, and biopolymers, such as peptides or oligonucleotides.

Combinatorial mixtures include, but are not limited to, collections of compounds, and libraries of compounds. These mixtures may be generated via combinatorial synthesis of mixtures or via admixture of individual compounds. Collections of compounds include, but are not limited to, sets of individual compounds or sets of mixtures or pools of compounds. These combinatorial libraries may be obtained from synthetic or from natural sources such as, for example to, microbial, plant, marine, viral and animal materials. Combinatorial libraries include at least about twenty compounds and as many as a thousands of individual compounds and potentially even more. When combinatorial libraries are mixtures of compounds these mixtures typically contain from 20 to 5000 compounds preferably from 50–1000, more preferably from 50–100. Combinations of from 100–500 are useful as are mixtures having from 500–1000 individual species. Typically, members of combinatorial libraries have molecular weight less than about 5000 Da.

The mass spectrometry techniques that may be used in the methods of this invention include all of the techniques and systems described herein or are subsequently developed. Tandem techniques are also useful, including combinations of all of the foregoing and LC/MS. The mass spectrometers used in the methods of this invention may be a single quadrupole, triple quadrupole, magnetic sector, quadrupole ion trap, time-of-flight instrument, and FTICR. Future modifications to mass spectrometry are expected to give rise to improved techniques which may also be useful herein.

EXAMPLES

Example 1

Determining the Structure of a 27-mer RNA Corresponding to the 16S rRNA A Site

In order to study the structure of the 27-mer RNA corresponding to the 16S rRNA A site, of sequence 5'-GGC-GUC-ACA-CCU-UCG-GGU-GAA-GUC-GCC-3' [SEQ. ID NO. 1] a chimeric RNA/DNA molecule that incorporates three deoxyadenosine (dA) residues at positions 7, 20 and 21 was prepared using standard nucleic acid synthesis protocols on an automated synthesizer. This chimeric nucleic acid of sequence 5'-GGC-GUC-dACA-CCU-UCG-GGU-GdAdA-GUC-GCC-3' [SEQ. ID NO. 2] was injected as a solution in water into an electrospray mass spectrometer. Electrospray ionization of the chimeric afforded a set of multiply charged ions from which the ion corresponding to the $(M-5H)^{5-}$ form of the nucleic acid was further studied by subjecting it to collisionally induced dissociation (CID). The ion was found to be cleaved by the CID to afford three fragments of m/z 1006.1, 1162.8 and 1066.2. These fragments correspond to the $w_7^{(2-)}$, $w_8^{(2-)}$ and the $a_7$-$B^{(2-)}$ fragments respectively, that are formed by cleavage of the chimeric nucleic acid adjacent to each of the incorporated dA residues.

The observation that cleavage and fragmentation of the chimeric RNA/DNA has occurred adjacent to all three dA sites indicates that the test RNA is not ordered around the locations where the dA residues were incorporated. Therefore, the test RNA is not structured at the 7, 20 and 21 positions.

A systematic series of chimeric RNA/DNA molecules is synthesized such that a variety of molecules, each incorporating deoxy residues at different site(s) in the RNA. All such RNA/DNA members are comixed into one solution. MS analysis, as described above, are conducted on the comixture to provide a complete map or 'footprint' that indicates the residues that are involved in secondary or tertiary structure and those residues that are not involved in any structure. See FIG. 1.

Example 2

Determining the Binding Site for Paromomycin on a 27-mer RNA Corresponding to the 16S rRNA A Site In order to study the binding of paromomycin to the RNA of example 1, the chimeric RNA/DNA molecule of example 1 was synthesized using standard automated nucleic acid synthesis protocols on an automated synthesizer. A sample of this nucleic acid was then subjected to ESI followed by CID in a mass spectrometer to afford the fragmentation pattern indicating a lack of structure at the sites of dA incorporation, as described in Example 1. This indicated the accessibility of these dA sites in the structure of the chimeric nucleic acid.

Next, another sample of the chimeric nucleic acid was treated with a solution of paromomycin and the resulting mixture analyzed by ESI followed by CID using a mass spectrometer. The electrospray ionization was found to produce a set of multiply charged ions that was different from that observed for the nucleic acid alone. This was also indicative of binding of the paromomycin to the chimeric nucleic acid, because of the increased mass of the observed ion complex. Further, there was also observed, a shift in the distribution of the multiply charged ion complexes which reflected a change in the conformation of the nucleic acid in the paromomycin-nucleic acid complex into a more compact structure.

Figure 2B:
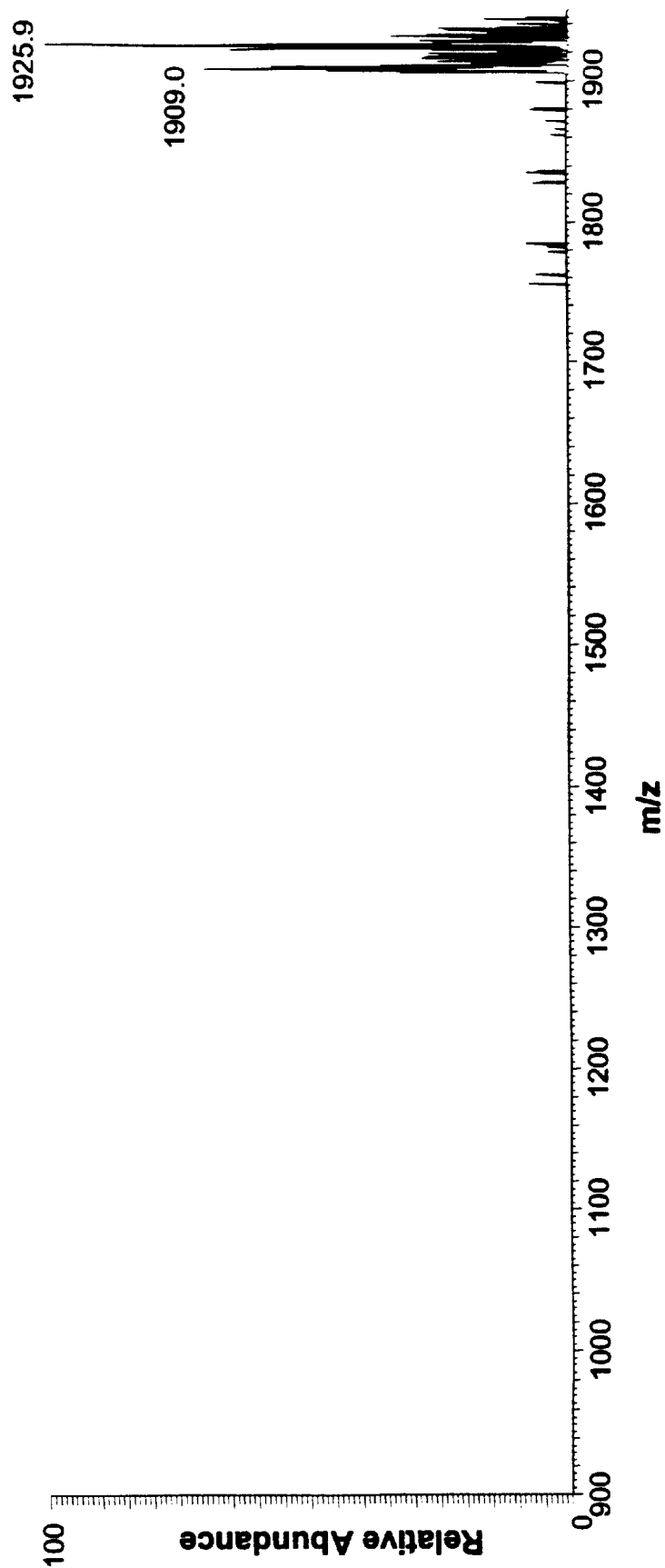

Cleavage and fragmentation of the complex by CID afforded information regarding the location of binding of the paromomycin to the chimeric nucleic acid. CID was found to produce no fragmentation at the dA sites in the nucleic acid. Thus paromomycin must bind at or near all three dA residues. Paromomycin therefore is believed to bind to the dA bulge in this RNA/DNA chimeric target, and induces a conformational change that protects all three dA residues from being cleaved during mass spectrometry. See FIGS. 2A and 2B.

Example 3

Determining the Identity of Members of a Combinatorial Library that Bind to a Biomolecular Target 1 µL (0.6 O.D.) of a solution of a 27-mer RNA containing 3 dA residues (from Example 1) was diluted into 500 uL of 1:1 isopropanol:water and adjusted to provide a solution that was 150 mM in ammonium acetate, Ph 7.4 and wherein the RNA concentration was 10 µM. To this solution was added an aliquot of a solution of paromomycin acetate to a concentration of 150 nM. This mixture was then subjected to ESI-MS and the ionization of the nucleic acid and its complex monitored in the mass spectrum. A peak corresponding to the $(M-5H)^{5-}$ ion of the paromomycin-27mer complex is observed at an m/z value of 1907.6. As expected, excess 27-mer is also observed in the mass spectrum as its $(M-5H)^{5-}$ peak at about 1784. The mass spectrum confirms the formation of only a 1:1 complex at 1907.6 (as would be expected from the addition of the masses of the 27-mer and paromomycin) and the absence of any bis complex that would be expected to appear at an m/z of 2036.5.

To the mixture of the 27-mer RNA/DNA chimeric and paromomycin was next added 0.7 μL of a 10 μM stock solution of a combinatorial library such that the final concentration of each member of the combinatorial library in this mixture with 27-mer target was ~150 nM. This mixture of the 27-mer, paromomycin and combinatorial compounds was next infused into an ESI-MS at a rate of 5 μL/min. and a total of 50 scans were summed (4 microscans each), with 2 minutes of signal averaging, to afford the mass spectrum of the mixture.

Figure 3A:
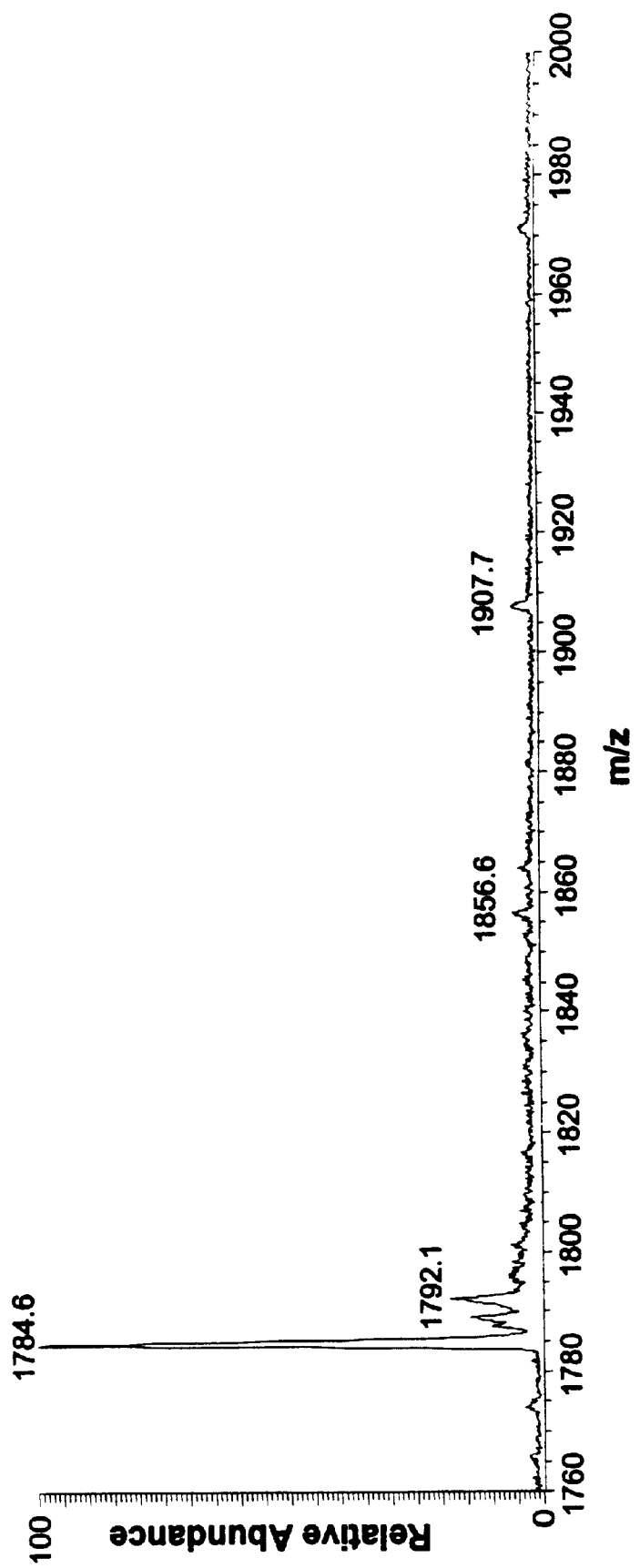
FIGS. 3A and 3B show the E-SI-MS of a 27-mer RNA/DNA hybrid target in the presence of paromorycin alone (FIG. 3A), and in the presence of both paromomycin and a combinatorial library (FIG. 3B).
Figure 3B:
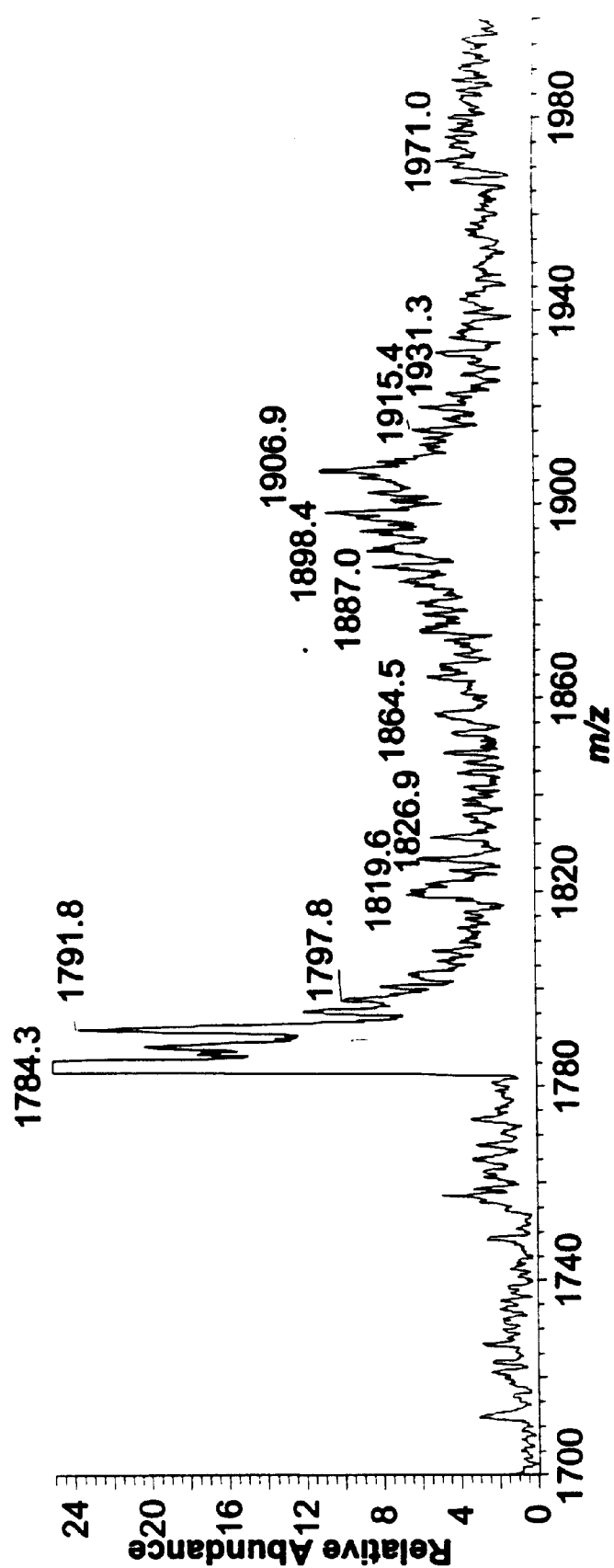

The ESI mass spectrum so obtained, shown in FIGS. 3A and 3B, demonstrated the presence of new signals for the $(M-5H)^{5-}$ ions at m/z values of 1897.8, 1891.3 and 1884.4. Comparing these new signals to the ion peak for the 27-mer alone the observed values of m/z; of those members of the combinatorial library that are binding to the target can be calculated. The masses of the binding members of the library were determined to be 566.5, 534.5 and 482.5, respectively. Knowing the structure of the scaffold, and substituents used in the generation of this library, it was possible to determine what substitution pattern (combination of substituents) was present in the binding molecules.

It was determined that the species of m/z 482.5, 534.5 and 566.5 would be the library members that bore the acetic acid+MPAC groups, the aromatic+piperidyl guanidine groups and the MPAC+guanidylethylamide groups, respectively. In this manner, if the composition of the combinatorial library is known a priori, then the identity of the binding components is straightforward to elucidate.

The use of FTMS instrumentation in such a procedure enhances both the sensitivity and the accuracy of the method. With FTMS, this method is able to significantly decrease the chemical noise observed during the electrospray mass spectrometry of these samples, thereby facilitating the detection of more binders that may be much weaker in their binding affinity. Further, using FTMS, the high resolution of the instrument provides accurate assessment of the mass of binding components of the combinatorial library and therefore direct determination of the identity of these components if the structural make up of the library is known.

Example 4

Determining the Site of Binding for Members of a Combinatorial Library that Bind to a Biomolecular Target The mixture of 27-mer RNA/DNA chimeric nucleic acid, as target, with paromomycin and the combinatorial library of compounds from Example 3 was subjected to the same ESI-MS method as described in Example 3. The ESI spectrum from Example 2 showed new signals arising from the complexes formed from binding of library members to the target, at m/z values of 1897.8, 1891.3 and 1884.4. The paromomycin-27mer complex ion was observed at an m/z of 1907.3.

Two complex ions were selected from this spectrum for further resolution to determine the site of binding of their component ligands on the 27-mer RNA/DNA chimeric. First, the ions at 1907.3, that correspond to the paromomycin-27mer complex, were isolated via an ion-isolation procedure and then subjected to CID. No cleavage was found to occur and no fragmentation was observed in the mass spectrum. This indicates that the paromomycin binds at or near in the bulged region of this nucleic acid where the three dA residues are present. Paromomycin therefore protects the dA residues in the complex from fragmentation by CID.

Figure 4:
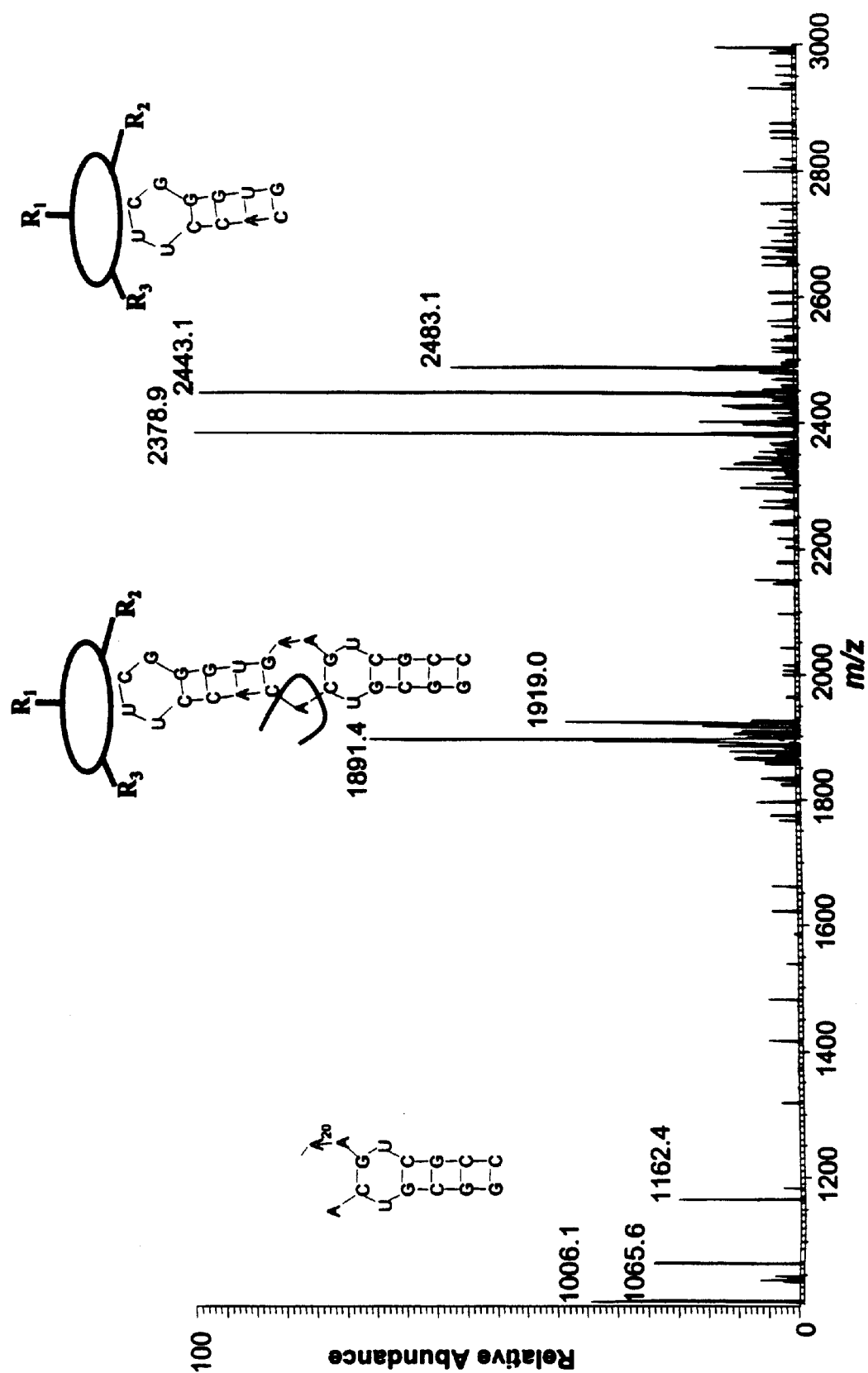
FIG. 4 shows the ESI-CID-MS spectrum of a combinatorial library member—27mer RNA/DNA hybrid noncovalent complex ion of m/z 1919.0.
Figure 5:
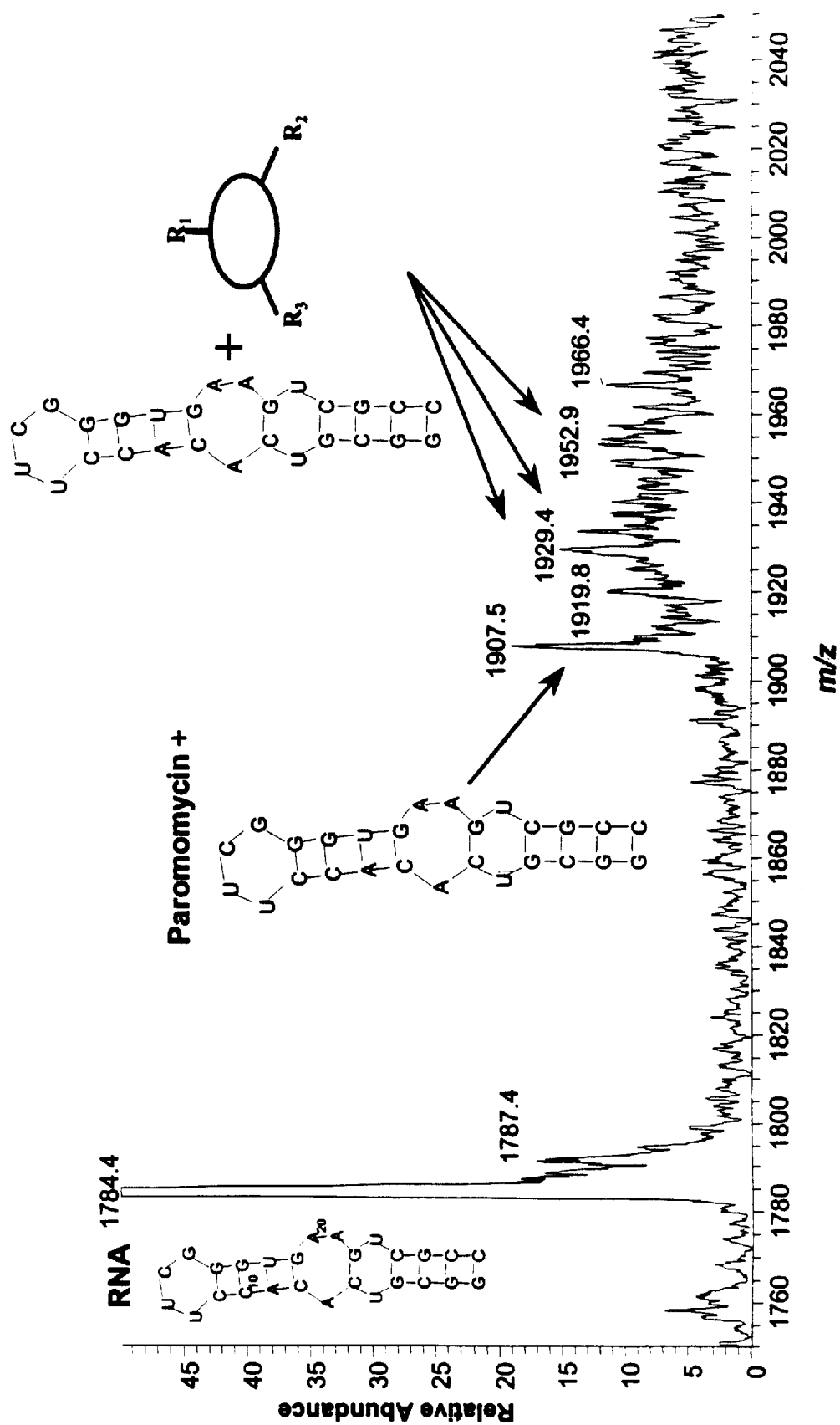
FIG. 5 shows the ESI-MS of a combinatorial library screened against a 27mer RNA/DNA hybrid.

Similarly, the ions at m/z 1897.8, that correspond to the complex of a library member with the 27mer target, were isolated via an ion-isolation procedure and then subjected to CID using the same conditions used for the previous complex, and the data was averaged for 3 minutes. The resulting mass spectrum (FIG. 4) revealed six major fragment ions at m/z values of 1005.8, 1065.6, 1162.8, 2341.1, 2406.3 and 2446.0. The three fragments at m/z 1005.8, 1065.6 and 1162.8 correspond to the $w_6^{(2-)}$, $a_7\text{-}B^{(2-)}$ and $w_{7(2-)}$ ions from the nucleic acid target. The three ions at higher masses of 2341.1, 2406.3 and 2446.0 correspond to the $a_{20}\text{-}B^{(3-)}$ ion+566 Da, $w_{21}^{(3-)}$ ion+566 Da and the $a_{21}\text{-}B^{(3-)}$ ion+566 Da. The data demonstrates at least two findings: first, since only the nucleic acid can be activated to give fragment ions in this ESI-CID experiment, the observation of new fragment ions indicates that the 1897.8 ion peak results from a library member bound to the nucleic acid target. Second, the library member has a molecular weight of 566. This library member binds to the GCUU tetraloop or the four base pairs in the stem structure of the nucleic acid target (the RNA/DNA chimeric corresponding to the 16S rRNA A site) and it does not bind to the bulged A site or the 6-base pair stem that contains the U*U mismatch pair of the nucleic acid target.

Further detail on the binding site of the library member can be gained by studying its interaction with and influence on fragmentation of target nucleic acid molecules where the positions of deoxynucleotide incorporation are different.

Example 5

Determining the Identity of a Member of a Combinatorial Library that Binds to a Biomolecular Target and the Location of Binding to the Target A 10 μM solution of the 27-mer RNA target, corresponding to the 16S rRNA A-site that contains 3 dA residues (from Example 1), in 100 mM ammonium acetate at pH 7.4 was treated with a solution of paromomycin acetate and an aliquot of a DMSO solution of a second combinatorial library to be screened. The amount of paromomycin added was adjusted to afford a final concentration of 150 nM. Likewise, the amount of DMSO solution of the library that was added was adjusted so that the final concentration of each of the 216 member components of the library was ~150 nM. The solution was infused into a Finnigan LCQ ion trap mass spectrometer and ionized by electrospray. A range of 1000–3000 m/z was scanned for ions of the nucleic acid target and its complexes generated from binding with paromomycin and members of the combinatorial library. Typically 200 scans were averaged for 5 minutes. The ions from the nucleic acid target were observed at m/z 1784.4 for the $(M-5H)^{5-}$ ion and 2230.8 for the $(M-4H)^{4-}$ ion. The paromomycin-nucleic acid complex was also observed as signals of the $(M-5H)^{5-}$ ion at m/z 1907.1 and the $(M-4H)^{4-}$ ion at m/z 2384.4 u.

Analysis of the spectrum for complexes of members of the combinatorial library and the nucleic acid target revealed several new signals that arise from the noncovalent binding of members of the library with the nucleic acid target. At least six signals for such noncovalent complexes were observed in the mass spectrum. Of these the signal at the lowest m/z value was found to be a very strong binder to the nucleic acid target. Comparison of the abundance of this ligand-nucleic acid complex ion with the abundance of the ion derived from the paromomycin-nucleic acid complex revealed a relative binding affinity (apparent $K_D$) that was similar to that for paromomycin.

MS/MS experiments, with ~6 minutes of signal averaging, were also performed on this complex to further establish the molecular weight of the bound ligand. A mass of 730.0±2 Da was determined, since the instrument performance was accurate only to ±1.5 Da. Based on this observed mass of the bound ligand and the known structures of the scaffold and substituents used in generating the combinatorial library, the structure of the ligand was determined to bear either of three possible combinations of substituents on the PAP5 scaffold. The MS/MS analysis of this complex also revealed weak protection of the dA residues of the hybrid RNA/DNA from CID cleavage. Observation of fragments with mass increases of 730 Da showed that the molecule binds to the upper stem-loop region of the rRNA target.

Example 6

Determining the Identity of Members of a Combinatorial Library that Bind to a Biomolecular Target and the Location of Binding to the Target A 10 μM solution of the 27-mer RNA target, corresponding to the 16S rRNA A-site that contains 3 dA residues (from Example 1), in 100 mM ammonium acetate at pH 7.4 was treated with a solution of paromomycin acetate and an aliquot of a DMSO solution of a third combinatorial library to be screened. The amount of paromomycin added was adjusted to afford a final concentration of 150 nM. Likewise, the amount of DMSO solution of the library that was added was adjusted so that the final concentration of each of the 216 member components of the library was ~150 nM. The solution was infused into a Finnigan LCQ ion trap mass spectrometer and ionized by electrospray. A range of 1000–3000 m/z was scanned for ions of the nucleic acid target and its complexes generated from binding with paromomycin and members of the combinatorial library. Typically 200 scans were averaged for 5 minutes. The ions from the nucleic acid target were observed at m/z 1784.4 for the $(M-5H)^{5-}$ ion and 2230.8 for the $(M-4H)^{4-}$ ion. The paromomycin-nucleic acid complex was also observed as signals of the $(M-5H)^{5-}$ ion at m/z 1907.1 and the $(M-4H)^{4-}$ ion at m/z 2384.4 u.

Analysis of the spectrum for complexes of members of the combinatorial library and the nucleic acid target revealed several new signals that arise from the noncovalent binding of members of the library with the nucleic acid target. At least two major signals for such noncovalent complexes were observed in the mass spectrum. MS/MS experiments, with ~6 minutes of signal averaging, were also performed on these two complexes to further establish the molecular weights of the bound ligands.

The first complex was found to arise from the binding of a molecule of mass 720.2±2 Da to the target. Two possible structures were deduced for this member of the combinatorial library based on the structure of the scaffold and substituents used to build the library. These include a structure of mass 720.4 and a structure of mass 721.1. MS/MS experiments on this ligand-target complex ion using CID demonstrated strong protection of the A residues in the bulge structure of the target. Therefore this ligand must bind strongly to the bulged dA residues of the RNA/DNA target.

Figure 6:
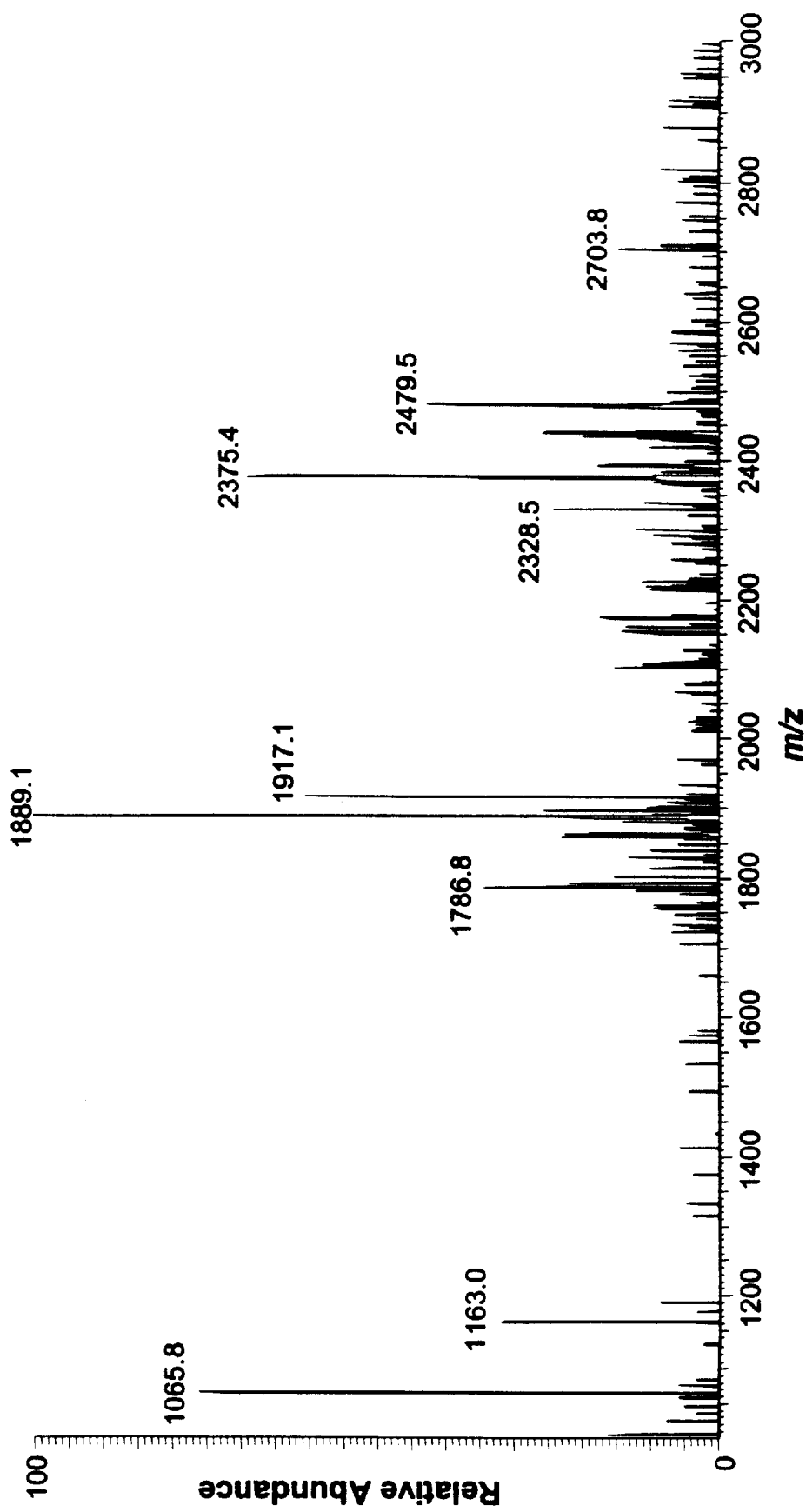
FIG. 6 shows the ESI-MS-MS analysis of the signal of m/z 1917.8 u arising from the binding of a member of mass 665 from another combinatorial library.
Figure 7:
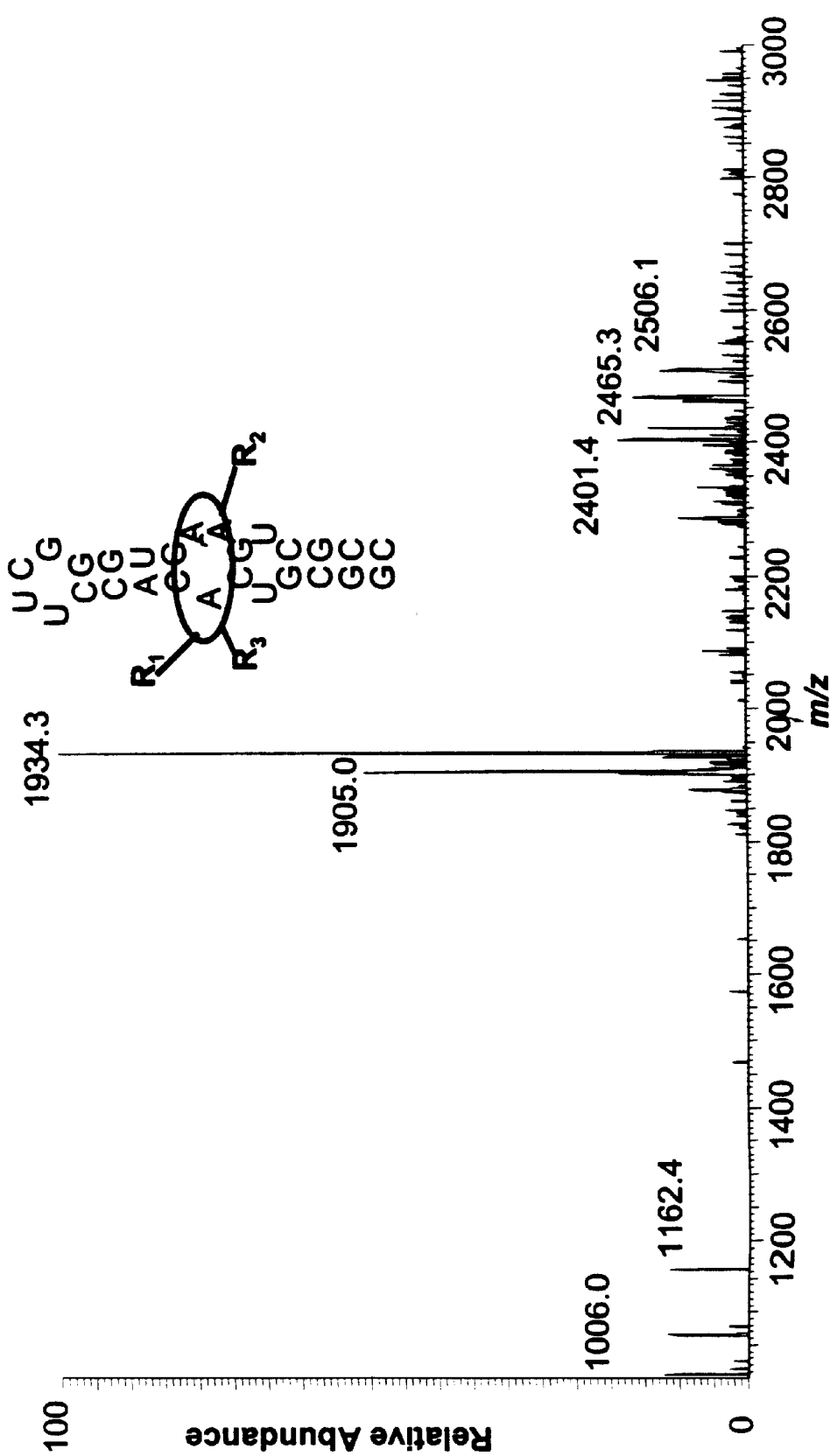
FIG. 7 shows the ESI-MS-MS analysis of the signal of m/z 1934.3 u arising from the binding of a member of mass 720 from a library.

The second major complex observed from the screening of this library was found to arise from the binding of a molecule of mass 665.2±2 Da to the target. Two possible structures were deduced for this member of the library based on the structure of the scaffold and substituents used to build the library. MS/MS experiments on this ligand-target complex ion using CID demonstrated strong fragmentation of the target. Therefore this ligand must not bind strongly to the bulged dA residues of the RNA/DNA target. Instead the fragmentation pattern, together with the observation of added mass bound to fragments from the loop portion of the target, suggest See FIG. 6. that this ligand must bind to residues in the loop region of the RNA/DNA target.

Example 7

Simultaneous Screening of a Combinatorial Library of Compounds against Two Nucleic Acid Targets The two RNA targets to be screened are synthesized using automated nucleic acid synthesizers. The first target (A) is the 27-mer RNA corresponding to the 16S rRNA A site and contains 3 dA residues, as in Example 1. The second target (B) is the 27-mer RNA bearing 3 dA residues, and is of identical base composition but completely scrambled sequence compared to target (A). Target (B) is modified in the last step of automated synthesis by the addition of a mass modifying tag, a polyethylene glycol (PEG) phosphoramidite to its 5'-terminus. This results in a mass increment of 3575 in target (B), which bears a mass modifying tag, compared to target (A).

A solution containing 10 μM target (A) and 10 μM mass modified target (B) is prepared by dissolving appropriate amounts of both targets into 100 mM ammonium acetate at pH 7.4. This solution is treated with a solution of paromomycin acetate and an aliquot of a DMSO solution of the combinatorial library to be screened. The amount of paromomycin added is adjusted to afford a final concentration of 150 nM. Likewise, the amount of DMSO solution of the library that is added is adjusted so that the final concentration of each of the 216 member components of the library is ~150 nM. The library members are molecules with masses in the 700–750 Da range. The solution is infused into a Finnigan LCQ ion trap mass spectrometer and ionized by electrospray. A range of 1000–3000 m/z is scanned for ions of the nucleic acid target and its complexes generated from binding with paromomycin and members of the combinatorial library. Typically 200 scans are averaged for 5 minutes.

The ions from the nucleic acid target (A) are observed at m/z 1486.8 for the $(M-6H)^{6-}$ ion, 1784.4 for the $(M-5H)^{5-}$ ion and 2230.8 for the $(M-4H)^{4-}$ ion. Signals from complexes of target (A) with members of the library are expected to occur with m/z values in the 1603.2–1611.6, 1924.4–1934.4 and 2405.8–2418.3 ranges.

Signals from complexes of the nucleic acid target (B), that bears a mass modifying PEG tag, with members of the combinatorial library are observed with m/z values in the 2199–2207.4, 2639–2649 and 3299–3311 ranges. Therefore, the signals of noncovalent complexes with target (B) are cleanly resolved from the signals of complexes arising from the first target (A). New signals observed in the mass spectrum are therefore readily assigned as arising from binding of a library member to either target (A) or target (B).

Extension of this mass modifying technique to larger numbers of targets via the use of unique, high molecular weight neutral and cationic polymers allows for the simultaneous screening of more than two targets against individual compounds or combinatorial libraries.

Example 8

Simultaneous Screening of a Combinatorial Library of Compounds against Two Peptide Targets The two peptide targets to be screened are synthesized using automated peptide synthesizers. The first target (A) is a 27-mer polypeptide of known sequence. The second target (B) is also a 27-mer polypeptide that is of identical amino acid composition but completely scrambled sequence compared to target (A). Target (B) is modified in the last step of automated synthesis by the addition of a mass modifying tag, a polyethylene glycol (PEG) chloroformate to its amino terminus. This results in a mass increment of ~3600 in target (B), which bears a mass modifying tag, compared to target (A).

A solution containing 10 $\mu$M target (A) and 10 $\mu$M mass modified target (B) is prepared by dissolving appropriate amounts of both targets into 100 mM ammonium acetate at pH 7.4. This solution is treated an aliquot of a DMSO solution of the combinatorial library to be screened. The amount of DMSO solution of the library that is added is adjusted so that the final concentration of each of the 216 member components of the library is ~150 nM. The library members are molecules with masses in the 700–750 Da range. The solution is infused into a Finnigan LCQ ion trap mass spectrometer and ionized by electrospray. A range of 1000–3000 m/z is scanned for ions of the polypeptide target and its complexes generated from binding with members of the combinatorial library. Typically 200 scans are averaged for 5 minutes.

The ions from the polypeptide target (A) and complexes of target (A) with members of the library are expected to occur at much lower m/z values that the signals from the polypeptide target (B), that bears a mass modifying PEG tag, and its complexes with members of the combinatorial library Therefore, the signals of noncovalent complexes with target (B) are cleanly resolved from the signals of complexes arising from the first target (A). New signals observed in the mass spectrum are therefore readily assigned as arising from binding of a library member to either target (A) or target (B). In this fashion, two or more peptide targets may be readily screened for binding against an individual compound or combinatorial library.

Example 9

Gas-phase Dissociation of Nucleic Acids for Determination of Structure

Nucleic acid duplexes can be transferred from solution to the gas phase as intact duplexes using electrospray ionization and detected using a Fourier transform, ion trap, quadrupole, time-of-flight, or magnetic sector mass spectrometer. The ions corresponding to a single charge state of the duplex can be isolated via resonance ejection, off-resonance excitation or similar methods known to those familiar in the art of mass spectrometry. Once isolated, these ions can be activated energetically via blackbody irradiation, infrared multiphoton dissociation, or collisional activation. This activation leads to dissociation of glycosidic bonds and the phosphate backbone, producing two series of fragment ions, called the w-series (having an intact 3'-terminus and a 5'-phosphate following internal cleavage) and the a-Base series (having an intact 5'-terminus and a 3'-furan). These product ions can be identified by measurement of their mass/charge ratio in an MS/MS experiment.

Figure 8:
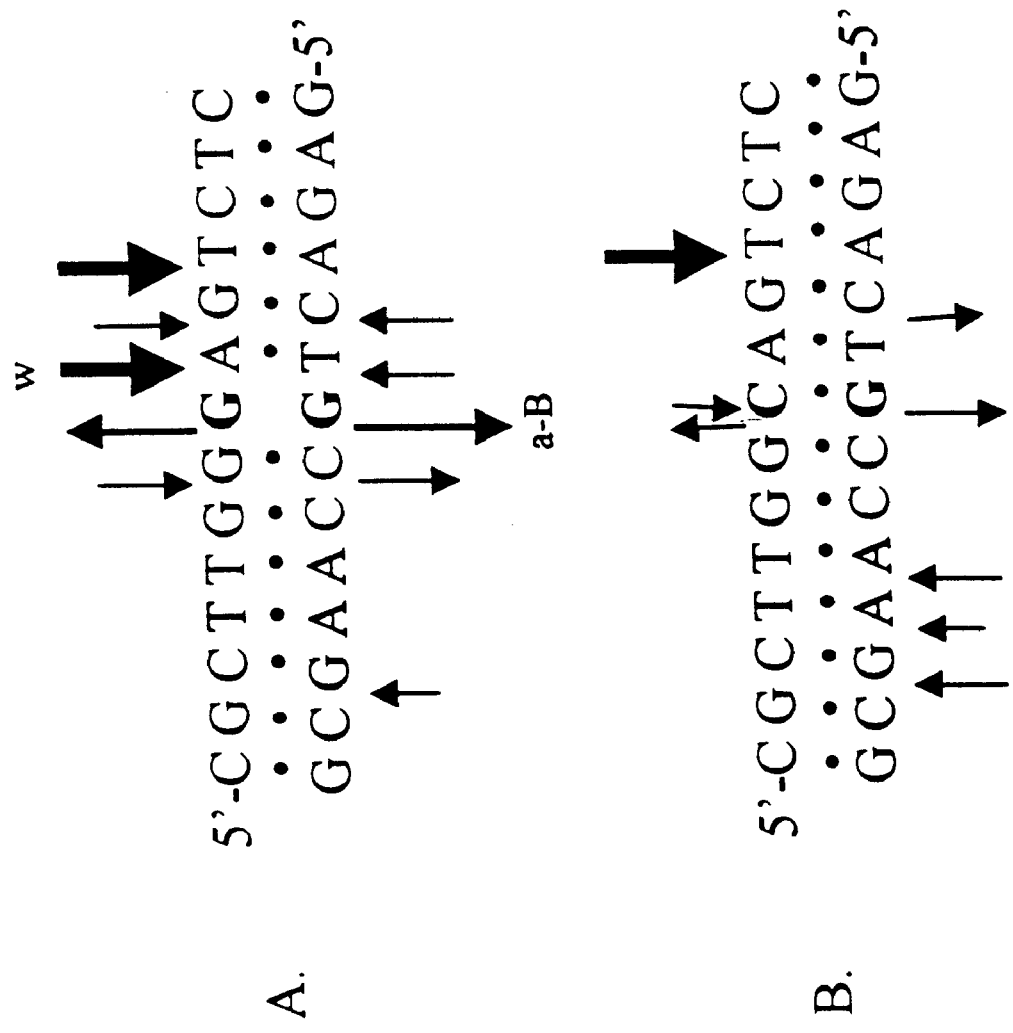
FIGS. 8 and 9 show graphical representations of the abundances of w and a-Base ions resulting from (CID) of ions from a DNA:DNA duplex.
Figure 9:
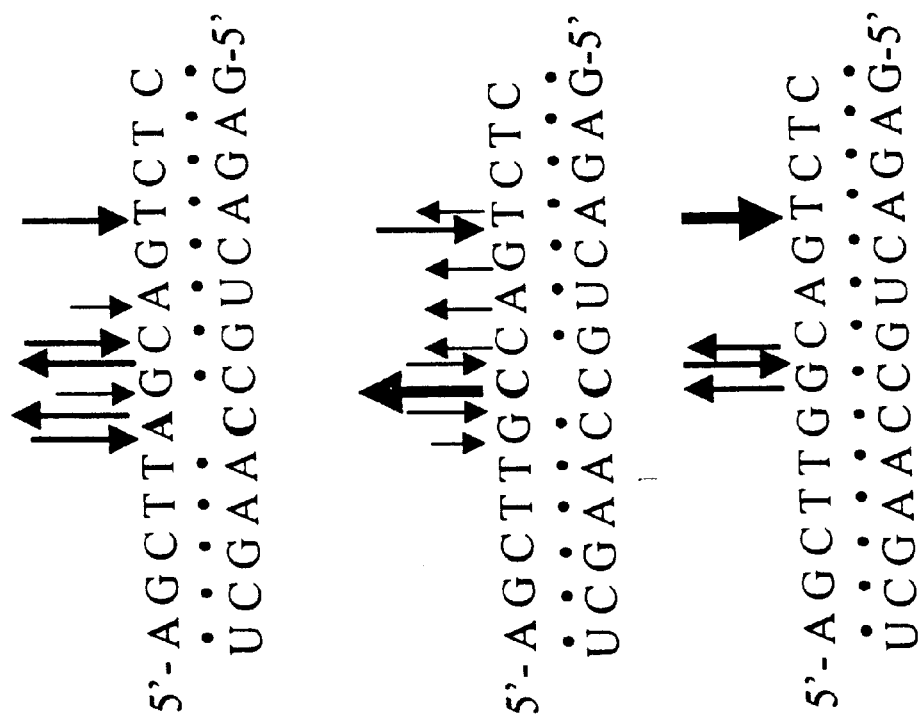

An example of the power of this method is presented in FIGS. 8 and 9. Shown in FIG. 8 part A is a graphical representation of the abundances of the w and a-Base ions resulting from collisional activation of the $(M-5H)^{5-}$ ions from a DNA:DNA duplex containing a G-G mismatch base pair. The w series ions are highlighted in black and point toward the duplex, while the a-Base series ions are highlighted in gray and point away from the duplex. The more abundant the fragment ion, the longer and thicker the respective arrow. Substantial fragmentation is observed in both strands adjacent to the mismatched base pair. The results obtained following collisional activation of the control DNA:DNA duplex ion is shown in FIG. 8 part B. Some product ions are common, but the pattern of fragmentation differs significantly from the duplex containing the mismatched base pair. Analysis of the fragment ions and the pattern of fragmentation allows the location of the mismatched base pair to be identified unambiguously. In addition, the results suggest that the gas phase structure of the duplex DNA ion is altered by the presence of the mismatched pair in a way which facilitates fragmentation following activation.

A second series of experiments with three DNA:RNA duplexes are presented in FIG. 9 In the upper figure, an A-C mismatched pair has been incorporated into the duplex. Extensive fragmentation producing w and a-Base ions is observed adjacent to the mismatched pair. However, the increased strength of the glycosidic bond in RNA limits the fragmentation of the RNA stand. Hence, the fragmentation is focused onto the DNA strand. In the central figure, a C-C mismatched base pair has been incorporated into the duplex, and enhanced fragmentation is observed at the site of the mismatched pair. As above, fragmentation of the RNA strand is reduced relative to the DNA strand. The lower figure contains the fragmentation observed for the control RNA:DNA duplex containing all complementary base pairs. A common fragmentation pattern is observed between the G5-T4 bases in all three cases. However, the extent of fragmentation is reduced in the complementary duplexes relative to the duplexes containing base pair mismatches.

Example 10

Figure 10:
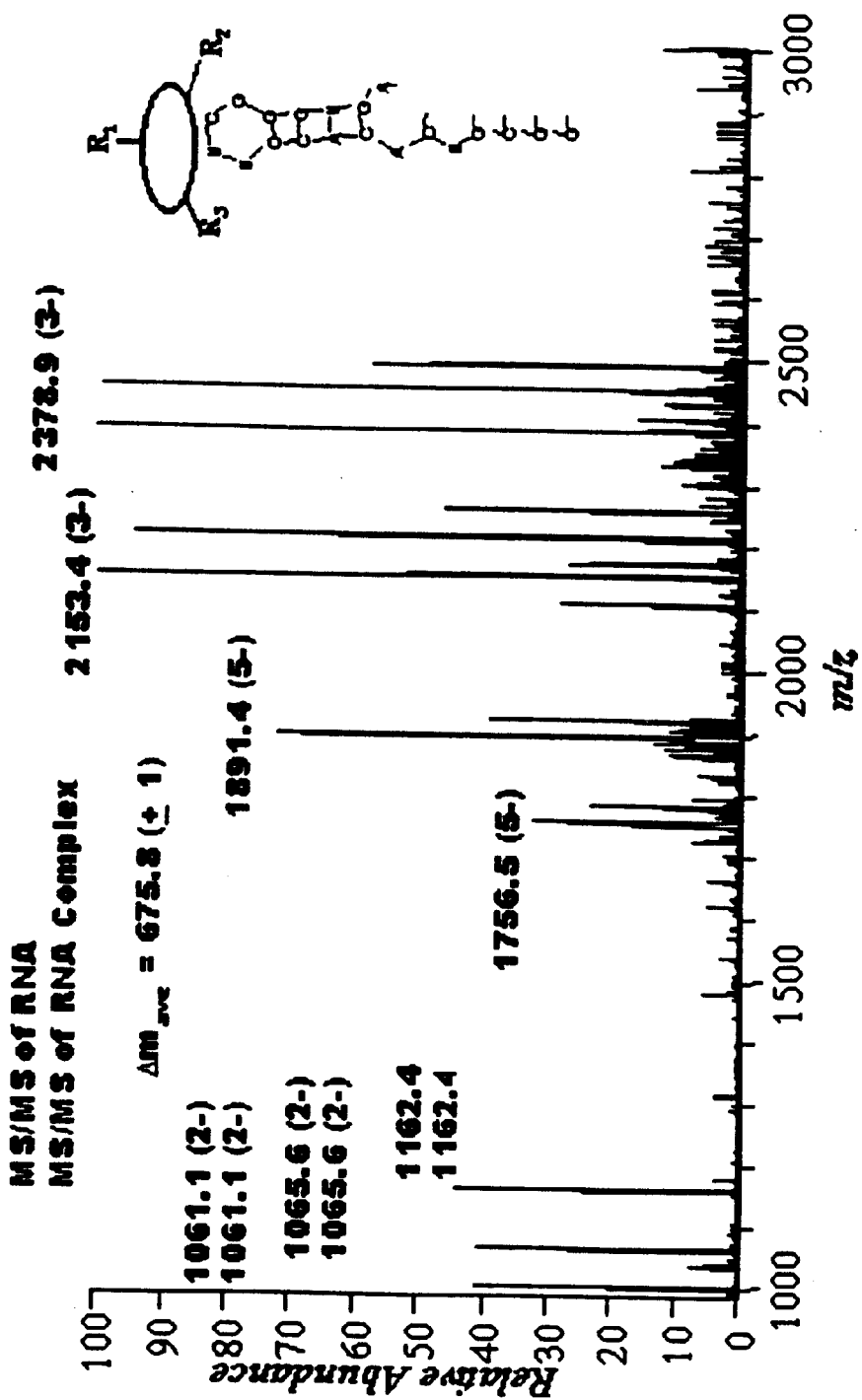
FIGS. 10, 11 and 12 depict MASS analyses to determine the binding of ligands to a molecular interaction site.
Figure 11:
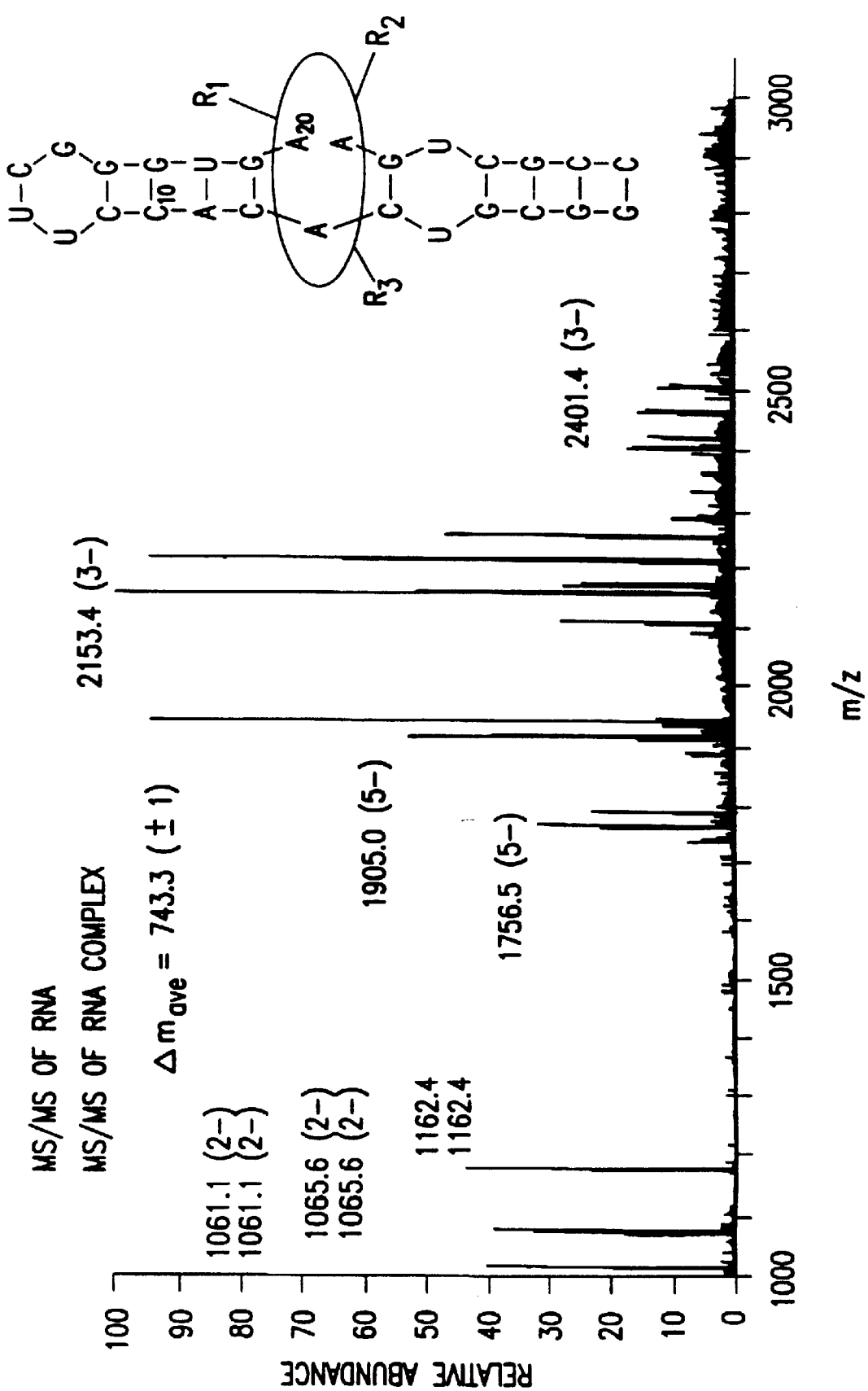

MASS Analysis of RNA—Ligand Complex to Determine Binding of Ligand to Molecular Interaction Site The ability to discern through mass spectroscopy whether or not a proposed ligand binds to a molecular interaction site of an RNA can be shown. FIGS. 10 and 11 depict the mass spectroscopy of an RNA segment having a stem-loop structure with a ligand, schematically illustrated by an unknown, functionalized molecule. The ligand is combined with the RNA fragment under conditions selected to facilitate binding and the result in complex is analyzed by a multi target affinity/specificity screening (MASS) protocol. This preferably employs electrospray ionization Fourier transform ion cyclotron resonance mass spectrometry as described hereinbefore and in the references cited herein. "Mass chromatography" as described above permits one to focus upon one bimolecular complex and to study the fragmentation of that one complex into characteristic ions. The situs of binding of ligand to RNA can, thus, be determined through the assessment of such fragments; the presence of fragments corresponding to molecular interaction site and ligand indicating the binding of that ligand to that molecular interaction site.

FIG. 10 depicts a MASS Analysis of a Binding Location for a non-A Site Binding molecule. The isolation through "mass chromatography" and subsequent dissociation of the (M–5H) 5– complex is observed at m/z 1919.8. The mass shift observed in select fragments relative to the fragmentation observed for the free RNA provides information about where the ligand is bound. The (2–) fragments observed below m/z 1200 correspond to the stem structure of the RNA; these fragments are not mass shifted upon Complexation. This is consistent with the ligand not binding to the stem structure.

FIG. 11 shows a MASS Analysis of Binding Location for the non-A Site Binding molecule. Isolation (i.e. "mass chromatography") and subsequent dissociation of the (M–5H)5– complex observed at m/z 1929.4 provides significant protection from fragmentation in the vicinity of the A-site. This is evidenced by the reduced abundance of the w and a-base fragment ions in the 2300–2500 m/z range. The mass shift observed in select fragments relative to the fragmentation observed for the free RNA provides information about where the ligand is bound. The exact molecular mass of the RNA can act as an internal or intrinsic mass label for identification of molecules bound to the RNA. The (2–) fragments observed below m/z 1200 correspond to the stem structure of the RNA. These fragments are not mass shifted upon Complexation—consistent with ligand not being bound to the stem structure. Accordingly, the location of binding of ligands to the RNA can be determined.

Example 11

Determination of Specificity and Affinity of Ligand Libraries to RNA Targets

A preferred first step of MASS screening involves mixing the RNA target (or targets) with a combinatorial library of ligands designed to bind to a specific site on the target molecule(s). Specific noncovalent complexes formed in solution between the target(s) and any library members are transferred into the gas phase and ionized by ESI. As described herein, from the measured mass difference between the complex and the free target, the identity of the binding ligand can be determined. The dissociation constant of the complex can be determined in two ways: if a ligand with a known binding affinity for the target is available, a relative Kd can be measured by using the known ligand as an internal control and measuring the abundance of the unknown complex to the abundance of the control, alternatively, if no internal control is available, Kd's can be determined by making a series of measurements at different ligand concentrations and deriving a Kd value from the "titration" curve.

Because screening preferably employs large numbers of similar, preferably combinatorially derived, compounds, it is preferred that in addition to determining whether something from the library binds the target, it is also determined which compound(s) are the ones which bind to the target. With highly precise mass measurements, the mass identity of an unknown ligand can be constrained to a unique elemental composition. This unique mass is referred to as the compound's "intrinsic mass label." For example, while there are a large number of elemental compositions which result in a molecular weight of approximately 615 Da, there is only one elemental composition ($C_{23}H_{45}N_5O_{14}$) consistent with a monoisotopic molecular weight of 615.2963012 Da. For example, the mass of a ligand (paromomycin in this example) which is noncovalently bound to the 16S A-site was determined to be 615.2969+0.0006 (mass measurement error of 1 ppm) using the free RNA as an internal mass standard. A mass measurement error of 100 ppm does not allow unambiguous compound assignment and is consistent with nearly 400 elemental compositions containing only atoms of C, H, N, and O. The isotopic distributions shown in the expanded views are primarily a result of the natural incorporation of 13C atoms; because high performance FTICR can easily resolve the 12C–13C mass difference we can use each component of the isotopic cluster as an internal mass standard. Additionally, as the theoretical isotope distribution of the free RNA can be accurately simulated, mass differences can be measured between "homoisotopic" species (in this example the mass difference is measured between species containing four 13C atoms).

Once the identity of a binding ligand is determined, the complex is isolated in the gas phase (i.e. "mass chromatography") and dissociated. By comparing the fragmentation patterns of the free target to that of the target complexed with a ligand, the ligand binding site can be determined. Dissociation of the complex is performed either by collisional activated dissociation (CAD) in which fragmentation is effected by high energy collisions with neutrals, or infrared multiphoton dissociation (IRMPD) in which photons from a high power IR laser cause fragmentation of the complex.

Figure 12:
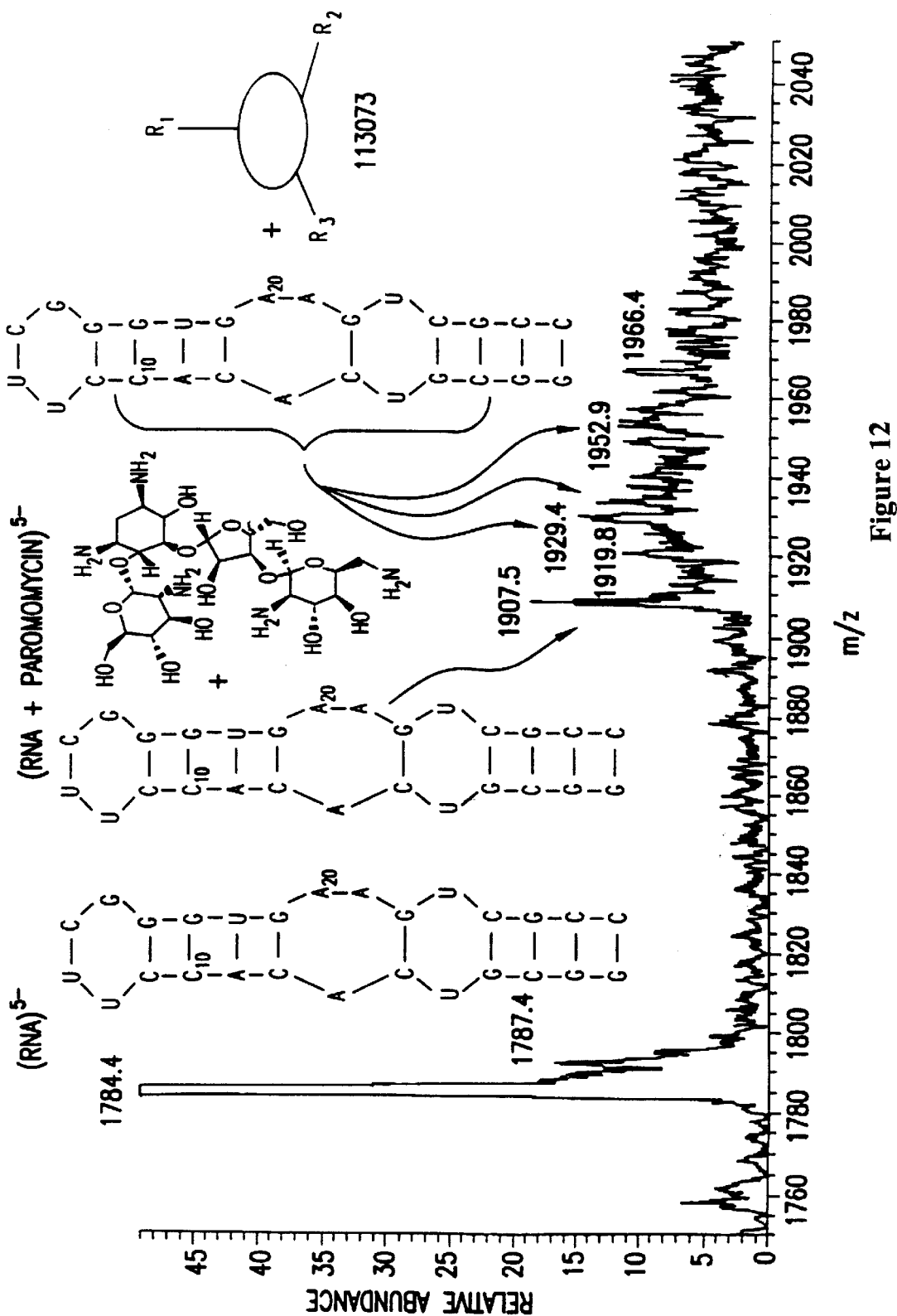
Figure 13:
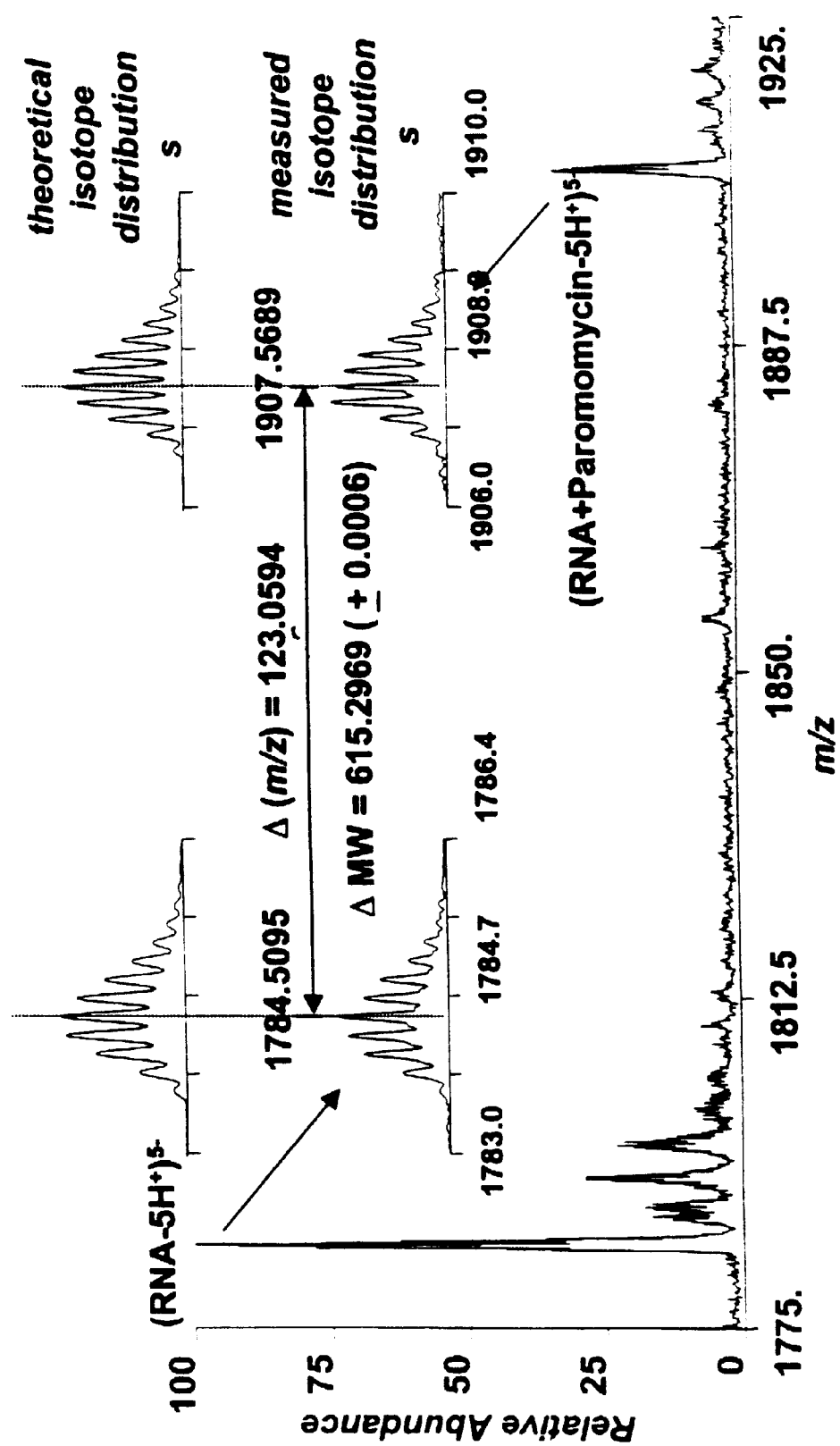
FIG. 13 depicts high precision ESI-FTICR mass measurement of the interaction of the 16S A site of an RNA complexed with paromomycin.

A 27-mer RNA containing the A-site of the 16S rRNA was chosen as a target for validation experiments. See FIG. 12. The aminoglycoside paromomycin is known to bind to the unpaired adenosine residues with a Kd of 200 nm and was used as an internal standard. The target was at an initial concentration of 10 mM while the paromomycin and each of the 216 library members were at an initial concentration of 150 nm. While this example was performed on a quadrupole ion trap which does not afford the high resolution or mass accuracy of the FTICR, it serves to illustrate the MASS concept. Molecular ions corresponding to the free RNA are observed at m/z 1784.4 (M–5H+)5– and 2230.8 4 (M–4H+) 4–. The signals from the RNA-paromomycin internal control are observed at m/z 1907.1 4 (M–5H+)5– and 2384.4 4 (M–4H+)4–. In addition to the expected paromomycin complex, a number of complexes are observed corresponding to binding of library members to the target. See FIG. 13.

One member of this library (MW=675.8+1.5) forms a strong complex with the target but MS/MS studies reveal that the ligand does not offer protection of A-site fragmentation and therefore binds to the loop region. Another member of Isis 113069 having an approximate mass of 743.8+1.5 demonstrates strong binding to the target and, as evidenced by MS/MS experiments provides protection of the unpaired A residues, consistent with binding at the A-site.

The rapid and parallel nature of the MASS approach allows large numbers of compounds to be screened against multiple targets simultaneously, resulting in greatly enhanced sample throughput and information content. In a single assay requiring less than minutes, MASS can screen 10 targets against a library containing over 500 components and report back which compounds bind to which targets, where they bind, and with what binding affinity.

What is claimed is:

1. A method for screening a plurality of biomolecular targets against a binding agent comprising:
   (a) providing n different biomolecular targets, wherein n is an integer greater than or equal to 2;
   (b) modifying n−1 of said biomolecular targets with mass modifying tags, wherein the mass to charge ratios of ions of about the same charge of said modified biomolecular targets are substantially distinguishable by mass spectrometry;
   (c) combining said modified biomolecular targets with a binding agent;
   (d) ionizing said combination from step (c) in a mass spectrometer to provide a plurality of ions, and
   (e) collecting mass spectral data from the ionization of step (d) and identifying therefrom ion abundances of said modified biomolecular targets and any complexes formed between said binding agent and said modified biomolecular targets.

2. The method of claim 1 wherein the ion abundances of said ions of said modified biomolecular target and said complexes are compared to determine the selectivity of the binding interaction between said ligand and said targets.

3. The method of claim 1 wherein said biomolecular target is a nucleic acid.

4. The method of claim 1 wherein said mass modifying tags are polymeric.

5. The method of claim 4 wherein said polymers are a polymers are a polythylene glycol, polypropylene, polystyrene, cellulose, sephadex, dextran, peptide or polyacrylamide.

6. The method of claim 3 wherein said mass modifying tag is attached to the 3'-terminus, 5'-terminus or sugar-phosphate backbone of said biomolecular targets.

7. A method for screening a plurality of biomoleculur targets against a combinatorial library of compounds comprising:
   (a) providing n different biomolecular targets, wherein n is an integer greater than or equal to 2;
   (b) modifying n−1 of said biomolecular targets with mass modifying tags, wherein the mass to charge ratios of ions of about the same charge of said modified biomolecular targets are substantially distinguishable by mass spectrometry;
   (c) combining said modified biomolecular targets with said combinatorial library of compounds;
   (d) ionizing said combination from step (c) in a mass spectrometer to provide a plurality of ions; and
   (e) collecting mass spectral data from the ionization of step (d) and identifying therefrom ion abundances of said modified biomolecular targets and any complexes formed between said compounds and said modified biomolecular targets.

8. The method of claim 7 wherein the ion abundances of said ions of said modified biomolecular target and said complexes are compared to determine the selectivity of the binding interactions between said compounds and said targets.

9. The method of claim 7 wherein said biomolecular target is a nucleic acid.

10. The method of claim 7 wherein said mass modifying tags are polymeric.

11. The method of claim 9 wherein said mass modifying tag is attached to the 3'-terminus, 5'-terminus or sugar-phosphate backbone of said biomolecular targets.

12. A method of screening multiple biomolecular targets against a ligand comprising:

(a) providing at least two biomolecular targets which possess different masses such that the mass to charge ratios of ions of about the same charge of said biomolecular targets are substantially distinguishable by mass spectrometry;

(b) combining said bimolecular targets with said ligand;

(c) ionizing said combination of step (b) in a mass spectrometer to form a plurality of ions, and (d) collecting mass spectral data from the ionization of step (c) and identifying therefrom ion abundances of said biomolecular targets and any complexes formed between said ligand and said biomolecular targets.

13. The method of claim 12 wherein said ion abundances of said biomolecular target and said complexes are compared to determine the selectivity of the binding interactions between said bimolecular targets and said ligand.

14. The method of claim 12 wherein said biomolecular target is a nucleic acid.

15. The method of claim 12 wherein said nucleic acid is derived from prokaryotic or eukaryotic nucleic acids.

16. The method of claim 12 wherein said biomolecular targets comprise a mixture of proteins.

* * * * *

SEQUENCE LISTING

```
<160> NUMBER OF SEQ ID NOS: 2

<210> SEQ ID NO 1
<211> LENGTH: 27
<212> TYPE: RNA
<213> ORGANISM: Artificial Sequence
<220> FEATURE:
<223> OTHER INFORMATION: Description of Artificial Sequence: Novel
      Sequence

<400> SEQUENCE: 1
ggcgucacac cuucggguga agucgcc                                      27

<210> SEQ ID NO 2
<211> LENGTH: 27
<212> TYPE: DNA
<213> ORGANISM: Artificial Sequence
<220> FEATURE:
<223> OTHER INFORMATION: Description of Combined DNA/RNA Molecule:
      Chimeric
<223> OTHER INFORMATION: Description of Artificial Sequence: Novel
      Sequence
<221> NAME/KEY: modified_base
<222> LOCATION: (7)
<223> OTHER INFORMATION: deoxyadenine
<221> NAME/KEY: modified_base
<222> LOCATION: (20)..(21)
<223> OTHER INFORMATION: deoxyadenine

<400> SEQUENCE: 2
ggcgucacac cuucggguga agucgcc                                      27
```